United States Patent
Toreki et al.

(10) Patent No.: US 6,780,507 B2
(45) Date of Patent: Aug. 24, 2004

(54) HYDROCAPSULES AND METHOD OF PREPARATION THEREOF

(75) Inventors: William Toreki, Gainesville, FL (US); Ara Manukian, Gainesville, FL (US); Rudolph Strohschein, Micopany, FL (US)

(73) Assignee: Analytical Research Systems, Inc., Gainesville, FL (US)

( * ) Notice: Subject to any disclaimer, the term of this patent is extended or adjusted under 35 U.S.C. 154(b) by 0 days.

(21) Appl. No.: 09/780,046

(22) Filed: Feb. 9, 2001

(65) Prior Publication Data

US 2002/0050659 A1 May 2, 2002

Related U.S. Application Data

(60) Provisional application No. 60/181,390, filed on Feb. 9, 2000.

(51) Int. Cl.[7] .......................... B32B 15/02; A01N 25/00
(52) U.S. Cl. .................... 428/402.21; 264/4.1; 264/4.3; 264/4.33; 264/4.7; 424/405; 424/408; 424/410; 424/490; 424/491; 428/402.22; 428/402.24; 428/403; 427/487
(58) Field of Search ......................... 264/4.1, 4.3, 4.33, 264/4.7; 424/405, 408, 410, 490, 491; 428/402.21, 402.22, 402.24, 403; 427/487

(56) References Cited

U.S. PATENT DOCUMENTS

| | | | | |
|---|---|---|---|---|
| 3,015,128 A | * | 1/1962 | Sommerville, Jr. | 264/3.5 |
| 3,310,612 A | * | 3/1967 | Somerville, Jr. | 264/4 |
| 3,389,194 A | * | 6/1968 | Somerville | 264/4 |
| 3,423,489 A | * | 1/1969 | Arens et al. | 264/4 |
| 3,779,842 A | * | 12/1973 | Grunwald et al. | 216/106 |
| 4,096,944 A | * | 6/1978 | Simpson | 106/784 |
| 4,178,366 A | * | 12/1979 | Bedding | 424/93.1 |
| 4,615,883 A | * | 10/1986 | Nelsen et al. | 119/6.7 |

(List continued on next page.)

FOREIGN PATENT DOCUMENTS

EP  0 778 083 A1  6/1997

OTHER PUBLICATIONS

XP002217445 & JP 03 060731 A, Mar. 15, 1991, Kinki et al., English Abstract.

Goodwin, John T., Somerville, George R., *Microencapsulation by physical methods*, CHEMTECH, Oct. 1974, pp. 623–626.

Thies, Curt, *Microencapsulation Mini Answer to Major Problems: Mocroencapsulation is a growing technology whose commercial potential for pharmaceutical, agricultural, and other applications is still being explored*, Todays Chemist at Work, Nov. 1994, pp. 40–45.

Cohen, Allen C., *Improved Method of Encapsulating Artificial Diet for Reading Predators of Harmful Insects*, Journal of Economic Entomology, Aug. 1983, vol. 76, No. 4, pp. 957–959.

Hagen, K.S. Tassan, R.L., *A method of Providing Artificial Diets to Chrysopa Larvae*, Journal of Economic Entomology, Oct. 1965, vol. 58, No. 5, pp. 999–1000.

*Primary Examiner*—Samuel A. Acquah
(74) *Attorney, Agent, or Firm*—Van Oyke & Assoc., P.A.

(57) ABSTRACT

A method is described for the formation of microcapsules which contain a liquid composition in the core, which is surrounded by a polymeric shell, membrane, or coating. The microcapsules are produced by simultaneously extruding the liquid core material along with a polymerizable liquid through concentrically-aligned nozzles to form spherically-layered biliquid droplets, followed by energy input in the form of heat or light which causes polymerization of the outer layer. The capsules formed by this method are capable of containing a variety of liquid materials having a composition ranging from completely aqueous to completely non-aqueous.

34 Claims, 7 Drawing Sheets

U.S. PATENT DOCUMENTS

| | | | |
|---|---|---|---|
| 4,701,326 A | * 10/1987 | Nelsen et al. | 119/6.7 |
| 4,744,988 A | * 5/1988 | Brox | 424/456 |
| 4,753,799 A | * 6/1988 | Nelsen et al. | 119/6.7 |
| 4,888,140 A | * 12/1989 | Schlameus et al. | 264/4.1 |
| 4,948,586 A | * 8/1990 | Bohm et al. | 424/406 |
| 5,225,279 A | * 7/1993 | Redlich et al. | 264/4.7 |
| 5,260,002 A | 11/1993 | Wang | |
| 5,277,979 A | * 1/1994 | Kielbania et al. | 264/4.3 |
| 5,364,634 A | * 11/1994 | Lew | 424/434 |
| 5,389,535 A | * 2/1995 | Aebischer et al. | 264/4 |
| 5,401,506 A | * 3/1995 | Chang et al. | 424/408 |
| 5,441,878 A | 8/1995 | Thies et al. | |
| 5,478,508 A | * 12/1995 | Suzuki et al. | 264/4 |
| 5,656,469 A | 8/1997 | Tresco et al. | |
| 5,690,869 A | 11/1997 | Hinterwaldner et al. | |
| 5,799,607 A | * 9/1998 | Greany et al. | 119/6.5 |
| 6,004,571 A | 12/1999 | Thies | |
| 6,165,615 A | 12/2000 | Itakura et al. | |
| 6,413,548 B1 | 7/2002 | Hamer et al. | |

* cited by examiner

HYDROCAPSULES AND METHOD OF PREPARATION THEREOF

CROSS REFERENCE TO RELATED APPLICATIONS

This application is a non-provisional application which claims priority under 35 U.S.C. section 120 to prior provisional application serial No. 60/181,390 filed on Feb. 9, 2000, and set to expire on Feb. 9, 2001.

BACKGROUND OF THE INVENTION

1. Field of the Invention

This invention relates to a novel method and apparatus for encapsulating discrete droplets of liquid by generating a continuous coating or layer of a polymerizable liquid which is substantially immiscible with the core liquid.

2. Background

Encapsulation refers to processes whereby an active ingredient is placed into a stabilized form in order to allow it to be conveniently stored, or protected from unfavorable conditions, until needed. The active ingredient may be dispersed in a protective matrix, or it may be surrounded by a coating, a shell, or a membrane. The release of active ingredient from the protected form may be rapid (such as by crushing, or by ingestion), or gradual (such as by dissolution, diffusion, or bio-degradation). In this manner it is possible to maximize the effectiveness of the active ingredient by ensuring that it is released at the proper time. This "controlled release" can also be made to occur over a programed time interval (sustained release), or on demand (stimulated release).

The term "microcapsule" has been used to describe small particles or beads, which range in size from less that one micron, up to several millimeters, which may contain a wide variety of active ingredients (Thies, 1994; Thies, 1987; Goodwin, 1974; Deasy, 1984; Hegenbart, 1993). Microcapsules can be divided into two broad groups: (1) "Aggregate" type microcapsules have the active ingredient dispersed uniformly throughout a continuous matrix. The matrix may be a solid dry polymer or a gel swollen with solvent. In the case where the gel is swollen with water, the term "hydrogel" is applied. Hydrogel encapsulation systems of this type are generally based on cross-linked forms of water-soluble polymers such as alginate, gelatin, pectin, agar, gellan, or starch (Sanderson, 1989). (2) "Mononuclear" microcapsules, on the other hand, consist of materials which show a true "shell-core" morphology. These are similar to an egg in that they have a solid shell or flexible membrane surrounding a core which may be a liquid, a solid, or even a gel.

Methods of producing microcapsules are the subject of several review articles (Sparks, 1981; Benita; 1996, Thies, 1994; Goodwin, 1974; Deasy, 1984; Hegenbart, 1993). Although numerous methods are described in these articles, the majority are simply not suitable for producing large (>500 micron diameter) mononuclear microcapsules which show a true shell-core morphology, and are capable of containing an aqueous-based solution as a core. Such capsules can be prepared with some degree of success, however, by using a method termed "concentric extrusion". In this approach to microcapsule manufacture, two mutually immiscible liquids are extruded through concentric orifices in order to produce a biliquid column, with the core fluid on the inside. Under the influence of gravitational or other forces, this biliquid column fragments into discrete droplets having a shell/core morphology. The liquid shell is then made to harden by some mechanism to give liquid-core microcapsules with a solid shell.

Hardening of the shell is generally effected either by heating to remove a solvent, or by cooling to solidify the molten shell material. The outer coating in these systems is often either a molten wax, or a solution of aqueous polymer such as gelatin or alginate. The use of heat, either to melt the shell material, or to drive off solvent, can be detrimental to sensitive core materials such as protein solutions or suspensions of living organisms. Similarly, the use of solvent-based shell formulations can lead to undesirable contamination of the core material, as well as health and safety concerns. Aqueous-based shell formulations such as gelatin cannot be used in conjunction with aqueous core materials since phase incompatibility is a necessary prerequisite for formation of a shell/core morphology using this technique. Also, these types of shells are, by nature, easily affected by water, and also very susceptible to dehydration. Another drawback of the existing techniques is that the physical and mechanical properties of the shell materials suitable for use in these approaches are limited. Waxes, for instance, have very poor elasticity and mechanical strength, and also low melt viscosity which makes production of very thin membranes impractical. Low molecular weight thermoplastic polymers are generally too brittle and lack the flexibility to give strong, thin-walled, individual capsules. In fact, very few polymeric shell materials have melting points low enough to make existing approaches widely practical. Thin, flexible, and durable membranes are generally only associated with crosslinked elastomeric polymers. By nature, such polymers are insoluble and will not melt even at extreme temperatures, so they cannot be used in liquid form. It has been demonstrated that even though some strong high molecular weight thermoplastic polymers have suitably low melting points, they tend to "fiberize" rather than give individual droplets when extruded through an orifice. Related microcapsule fabrication techniques such as "centrifugal extrusion" suffer from similar drawbacks.

Examples of these existing techniques and their shortcomings can be found in various U.S. patents. Probably the first use of concentric fluid streams to accomplish the encapsulation of liquid agents was described in U.S. Pat. No. 2,275,154 (Merrill et al., Mar. 3, 1942). In that invention a medicinal component is surrounded by gelatin in a liquid form, and then the gelatin is caused to harden. Since gelatin is soluble in water, this method is useless for the encapsulation of aqueous liquids.

Similar methods are reported in the following U.S. Pat. No. 2,766,478 (Raley et al., Oct. 16, 1956); U.S. Pat. No. 2,799,897 (Jansen et al., Jul. 23, 1957); U.S. Pat. No. 2,911,672 (van Erven Dorens, Nov. 10, 1959); U.S. Pat. No. 3,015,128 (Somerville, Jan. 2, 1962); U.S. Pat. No. 3,310,612 (Somerville, Mar. 21, 1967); U.S. Pat. No. 3,389,194 (Somerville, Jun. 18, 1968); U.S. Pat. No. 3,423,489 (Arens et al., Jan. 21, 1969); and U.S. Pat. No. 3,779,942 (Bolles, Dec. 18, 1973). The shortcomings of these methods are described above, and are also discussed in U.S. Pat. No. 3,423,489. More recently, these shortcomings have been discussed in U.S. Pat. No. 5,478,508 (Suzuki et al., Dec. 26, 1995). This patent fails to successfully overcome the stated shortcomings, as it utilizes materials such as waxes, oils, fats, paraffins, thermoplastic resins, gelatin, or other water-soluble polymers for the shell material. The insufficiencies of these coatings have been described above.

Currently, there is a small specialty market for the sale of beneficial insects (such as lady beetles and parasitic wasps)

for use in pest control on high value crops, such as greenhouses and nurseries producing "organically-grown" produce. Since the cost of naturally-produced beneficial insects is high, the resulting "green" produce that goes to market is sold only to a small number of customers willing to pay substantially higher prices. While mass rearing of phytophagous insects (plant feeding insects) is well developed and has been implemented in most entomological research organizations world-wide, mass rearing of entomophagous insects (insects that eat other insects) generally lags far behind. The reason for this large gap in rearing methods has been largely due to the lack of a suitable artificial substitute for the natural insect host diet. Although useful liquid diet formulations are currently being developed, there exist no suitable technologies for incorporating these aqueous-based liquid diets into practical forms for storage and presentation. Liquid-core hydrocapsules are a promising solution to this problem.

A laboratory method for encapsulating artificial diet for rearing predators of harmful insects by forming a paraffin coating over an artificial liquid diet has been described by Hagen and Tassan (1965). This method utilized a molten waxy polymer for the coating material, and as such it has limited utility. Also, only a few hundred coated droplets could be produced per day, as the method was very labor intensive, and thus not practical for large-scale mass rearing. An improvement over the Hagen and Tassan method was developed by Cohen (1983) for producing paraffin coated artificial diet capsules. This method lends itself to improved uniformity of the droplet size and efficiency in formation. The main drawback, however, is that the method required some care and patience on the part of the technician, who could produce no more than 2–3,000 capsules per day. Thus, the technique is not suitable for mass production rearing, but simply useful as a research tool.

The closest commercial application to what is needed for production of individual artificial diet capsules that are suitable for use in general beneficial insect rearing is a process which produces 1–2 mm diameter wax-based coated artificial diet for *Chrysoperla carnea* (green lacewing) predators. This method is based on earlier procedures developed by Martin et al. (Martin, 1978). This encapsulated diet is not suitable for general mass rearing for several reasons: The diet coating melts at temperatures above 28° C., which is slightly above indoor room temperature, and would be unusable in warm incubators, greenhouses, or outdoors in even the mildest of growing regions. The size of the capsules produced are too small to contain sufficient diet for optimal rearing of many predators and parasitoids. The wax coating cannot withstand rough handling nor packing in large containers, which could cause these tiny wax capsules to crush or leak. The biggest limitation to the wax coating used, is that it cannot contain any insect diet with a high lipid (fat) content, such as the USDA's DI-DIET (see U.S. Pat. No. 5,799,607, Sep. 1, 1998, Greany et al.). The lipids act as a solvent which decomposes the wax coating causing the capsule to leak. Currently, an ideal encapsulation system is not available. Such a system would need to meet the following criteria: be acceptable for feeding by the insects of concern; be penetrable by the feeding insect; not be deleterious to the feeding insect; not interact negatively with, or alter the properties of the artificial diet; maintain integrity at ambient temperature; contain an aqueous solution without dissolving; prevent desiccation of the liquid diet; allow itself to be formed or applied in various thicknesses; permit any 3-D geometric shape, generally spherical in nature; be suitable for various sizes, ca.1.0 cm±0.5 cm; withstand sterilization by irradiation (or other means), which is necessary for long term storage.

There are no existing methods applicable for the mass-production of soft-shelled, water-filled, 1 to 10 mm diameter capsules which can be used to encapsulate aqueous artificial diets (or any water-based solution). Industrial encapsulation technologies in use today (developed for the needs of the biomedical, pharmaceutical, and food industries), generally produce microcapsules that are too small ($\leq 50$ μm), or too hard, or are made of materials that are unsuitable for a wide variety of applications. Many of these methods rely on water to dissolve the capsule material in order to release its contents, (such as in the human stomach). Obviously, such methods are not well suited for containing aqueous-based liquids. U.S. Pat. No. 4,096,944 (Simpson, Jun. 27, 1978) describes a method which utilizes microcapsules having diameters in a range of 400 to 5000 microns, with inert, frangible shells enclosing droplets of liquid water. These microcapsules may have some suitability for the applications described therein; however they are made in accordance with the method disclosed in U.S. Pat. No. 3,389,194 (discussed above), and as such they are not broadly useful for the aforementioned reasons.

One proven approach for chemical-alternative insecticides is the use of insect pathogens or "entomopathogens" as a bio-rational method of controlling pests. Entomopathogens are naturally-occurring disease-causing organisms such as protozoa, bacteria, fungi, and nematodes which specifically infect or vector other harmful agents (such as endotoxins) into insects causing death or disruption of its life cycle. They are very good candidates for use as bio-pesticides since most insect pathogens are specific to certain groups of insects or certain life stages of insects. Additionally, microbial entomopathogens generally do not directly affect beneficial insects and are non-toxic to wildlife or humans (Weeden et al., 1996; Hoffmann and Frodsham, 1993). Entomopathogens generally infect their host (pest) insects through ingestion or by direct contact with an organism. In either case, once the pathogen has entered the insect, it will eventually lead to the insect's death or decreased activity of the pest. Widespread use of this type of pest control strategy has been stifled greatly by the lack of suitable methods for delivery of entomopathogens into the environment. Most entomopathogenic organisms are extremely sensitive to adverse environmental conditions. Packaging of microorganisms in the form of microcapsules can provide extended useful lifetimes by protecting them from harsh conditions such as sunlight and low humidity.

The same capsules which are useful in the mass-rearing of beneficial insects can be converted into lethal snacks for pest insects, simply by incorporation of entomopathogenic agents into the aqueous core. For applications such as cockroach and fire ant baits, it is not necessary that the shell be soft enough to allow the entrapped organisms to escape on their own, since the shells can be easily breached by the feeding insect. In fact, the capsule can serve as a convenient package which allows the target insect to carry the infective agent directly into its nest. This behavior has been observed in studies involving wild fire ants feeding on encapsulated artificial diet prepared using the method of the current invention. Incentive to feed on the capsules can also be provided by incorporation of essential nutrients, or by the addition of feeding stimulants or kairomones. For more passive delivery approaches, it is possible to adjust the shell formulation to the needs of a particular system, so that the entomopathogenic agent can emerge without direct contact between the insect and the microcapsule. In fact, a combination of the two release mechanisms can serve to be the most effective approach in some cases. Other uses for microencapsulated microorganisms are possible as well. Some of these applications would include: fermentation processes, herbicides, medical, veterinary, and horticultural uses.

There are several reports in the literature concerning the microencapsulation of bio-control microorganisms in continuous-matrix hydrogels. These processes do not result in actual shell-core microcapsules as discussed above. Instead, they result in soft, hydrated gel particles which are essentially a uniform distribution of active organisms trapped in a hydrogel matrix, rather than a contained liquid suspension of organisms. These hydrogels have a very high water content (up to 90%), and thus they are very susceptible to dessication. They also serve as prime breeding grounds for non-desirable contamination by ambient microorganisms. This type of hydrogel-entrapment method has been used for the encapsulation biocontrol fungi such as Trichoderma, Gliocladium, Alternaria, and Penicillium into alginate-clay matrices for use as mycoherbicides (Walker, 1983; Fravel, 1985). The alginate hydrogel particles were then dried to produce hard pellets. This delivery system was found to be somewhat effective, but subsequent bacterial contamination of the pellets was apparent. Such contamination is no doubt facilitated by the porous and hygroscopic nature of the entrapping polymer. A true shell-core type of microcapsule having an aqueous interior surrounded by a protective membrane, rather than simply a gel matrix would help to prevent this.

A substantially similar method for encapsulating Steinernematid and Heterohabditid nematodes has been reported (Kaya, 1985; 1987). This work serves as the basis for the following U.S. Pat. No. 4,615,883 (Nelsen et al., Oct. 7, 1986); U.S. Pat. No. 4,701,326 (Nelsen et al., Oct. 20, 1987); and U.S. Pat. No. 4,753,799 (Nelsen et al., Jun. 28, 1988). The survival rate and pathogenicity of the nematodes remained high throughout the encapsulation process, but dessication during storage proved to be a problem. Attempts have been made to reduce the rate of evaporation of the aqueous carrier by coating these continuous-matrix capsules with hydrocarbon oils or greases, as described in U.S. Pat. No. 4,178,366 (Bedding, Dec. 11, 1979) and U.S. Pat. No. 5,401,506 (Chang et al., Mar. 28, 1995).

A method of encapsulating cells in a tubular extrudate is described in U.S. Pat. No. 5,389,535 (Aebischer, et al., Feb. 14, 1995). The cells are encapsulated within a semipermeable polymeric membrane by co-extruding an aqueous cell suspension and a polymer solution through a common port to form a tubular extrudate having a polymeric outer coating. The cell suspension and the polymeric solution can be extruded through a common extrusion port having at least two concentric bores, such that the cell suspension is extruded through the inner bore and the polymeric solution is extruded through the outer bore. The polymeric solution coagulates to form an outer coating. As the outer coating is formed, the ends of the tubular extrudate can be sealed to form a cell capsule. In one embodiment, the tubular extrudate is sealed at intervals to define separate cell compartments connected by polymeric links. This method is not suitable for the production of discrete microcapsules. Also, the semipermeable membranes produced by this method are not suitable for long term storage without dessication.

U.S. Pat. No. 5,364,634 (Lew, Nov. 15, 1994) described a controlled-release pH-sensitive capsule. The microcapsules are made by methods well known in the art (such as centrifugal extrusion), and as such are subject to the limitations described above. Similar limitations are encountered in the method of U.S. Pat. No. 4,888,140 (Schlameus et al., Dec. 19, 1989) which describes forming fluid filled microcapsules by the simultaneous extrusion of core and shell material from coaxially aligned and concentric extrusion nozzles into a surrounding carrier fluid. In this method an aqueous polymer such as gelatin is used as the shell material. The limitations of such materials have been described above. U.S. Pat. No. 4,948,586 (Bohm et al., Aug. 14, 1990) describes a method for producing microencapsulated insecticidal pathogens. This method is based upon emulsion formation, and the product is described by the inventor as "analogous to gelatin balls". It does not yield discrete microcapsules having a shell/core morphology and a liquid center.

The current invention allows one to produce capsules that are of the shellcore type, and consist of a polymer membrane surrounding a liquid center. An important feature of these mononuclear microcapsules is that they contain a water-based core. Other types of processes, such as the familiar "softgel" technology used to encapsulate vitamin E are not suitable for encapsulating aqueous liquids (Rose, 1987). These types of methods are described, for instance, in U.S. Pat. No. 4,744,988 (Brox, Dec. 19, 1989). The shell materials resulting from the unique encapsulation process described in the current patent disclosure are crosslinked hydrophobic elastomeric polymer networks. These shells are produced via the ultraviolet (UV)-initiated free-radical copolymerization of functionalized prepolymers (silicones, urethanes, epoxys, polyesters, etc.) and/or vinyl monomers such as acrylates. Because the structure of the polymer shell of these types of capsules is very distinct from the softgels or aggregate-type hydrogel microcapsules described above, they are referred to as "HYDROCAPSULES™". This implies that they have an aqueous liquid core surrounded by a thin hydrophobic polymer membrane. However, further research has demonstrated that this encapsulation process also has utility for encapsulating liquids other than "aqueous compositions". The same method used for encapsulating "aqueous compositions" has been utilized to encapsulate oils and alcohols. These "non aqueous compositions", are able to be encapsulated because they too are substantially immiscible with the shell-forming polymerizable liquid.

This encapsulation process has other potential applications in the agricultural community, and in the biomedical and chemical industries. The current invention enables the production of small liquid-containing polymer capsules, that have good chemical resistance to many organic solvents, and are capable of containing many types of active ingredients for use in a wide range of applications including (but not limited to): food sources for other insects used in laboratory research; poison baits for pest insects (such as roaches or fire ants) which could safely contain toxins combined with a phagostimulant or other attractant ("attracticide" approach); pheromone release for insect mating disruption; controlled pheromone release for traps used in insect population monitoring; water-soluble drug, medicine, or microbial dispensing systems; or for encapsulation of foodstuffs or flavoring ingredients, and similar applications.

SUMMARY OF THE INVENTION

A method is disclosed for encapsulating discrete droplets of liquid by generating a continuous coating or layer of a polymerizable liquid which is substantially immiscible with the core liquid. The polymerizable liquid is made to surround discrete droplets of the core liquid and is made to polymerize to form a shell, membrane, or solid coating around the discrete droplet core liquid. Methods of making and using the encapsulated liquid as well as an apparatus for making the hydrocapsules are also disclosed.

DETAILED DESCRIPTION OF THE PREFERRED EMBODIMENT

The process of co-extrusion involves ejecting two liquid streams from concentric nozzles under a force. In this manner, the liquid solution to be encapsulated and an immiscible shell-forming organic liquid are pushed simultaneously through concentric nozzles by force. The center nozzle carries the material to be encapsulated (liquid), while the outer nozzle carries the coating precursor (generally a mixture of vinyl monomers or vinyl-functionalized prepolymers).

Figure 1:
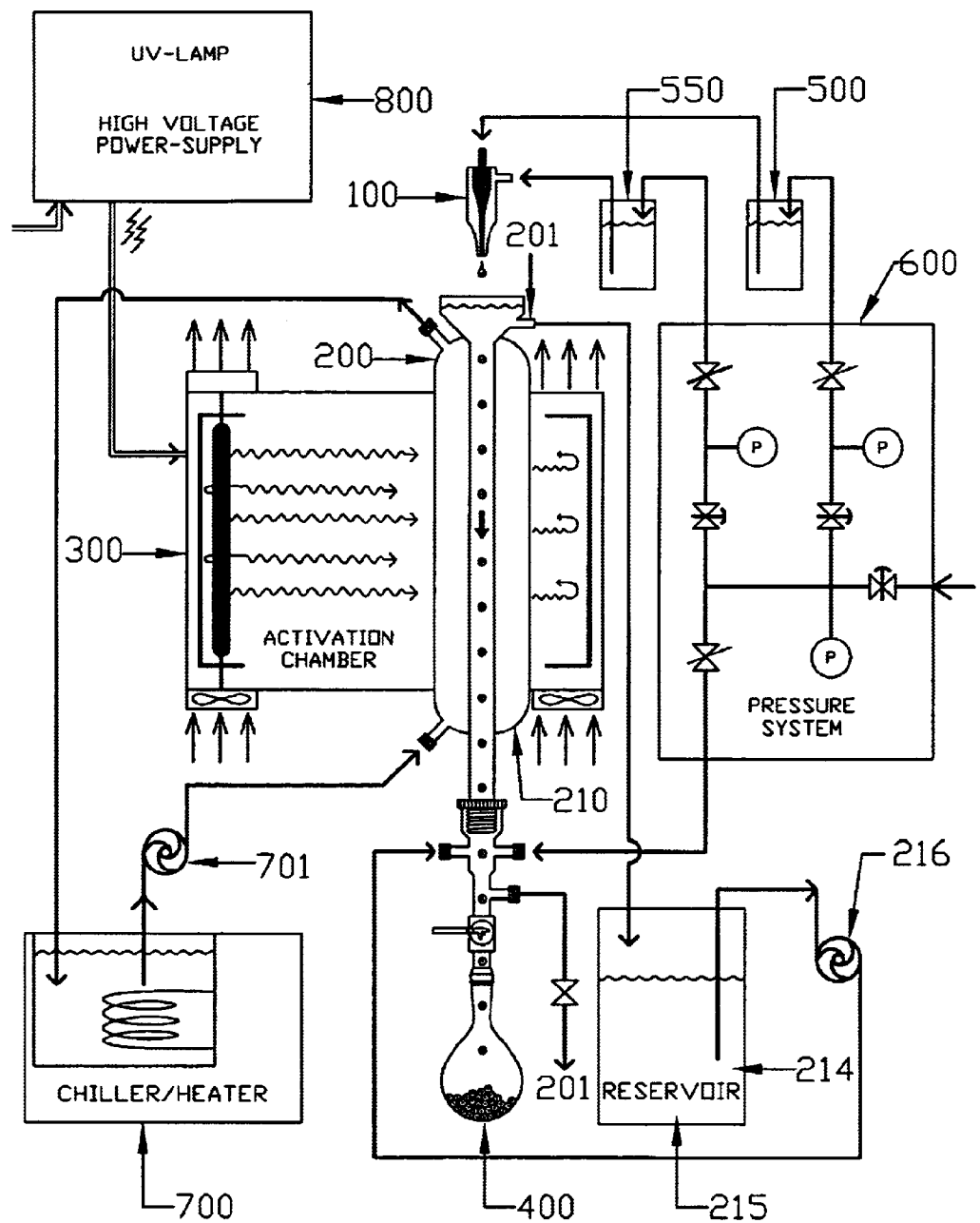
FIG. 1: Arrangement of whole system.

FIG. 1 depicts the entire hydrocapsule system. The concentric nozzle 100 is made up of two chambers that simultaneously release the core material and the coating material. The activation column 200, contains a suspending fluid surrounded by a water jacket to allow transfer of heat into and out of the reaction zone. The drain 201 is used to clear suspending fluid if necessary. The column fluid reservoir 215 and the column fluid pump 216 circulate the suspending fluid 214 and regulate the level of the suspending fluid 214 retained inside the activation column 200. The activation chamber 300 provides the use of ultra-violet (UV) light to promote polymerization of vinyl monomers, oligomers, and/or crosslinking agents, which are principal components of the shell formulations of this invention. The receiver 400 accepts and retains the polymerized hydrocapsules. The reservoirs 500 and 550 contain the core material and the coating material respectively. The pressure system 600 can be used for filtration, pressure regulation and flow control of all gases and fluids used in the co-extrusion process. The chiller/heater unit 700 and the column coolant pump 701 regulate the activation column temperature and allow the transfer of heat into and out of the reaction zone. The high voltage power supply 800 supplies energy to the activation chamber 300.

Figure 2:
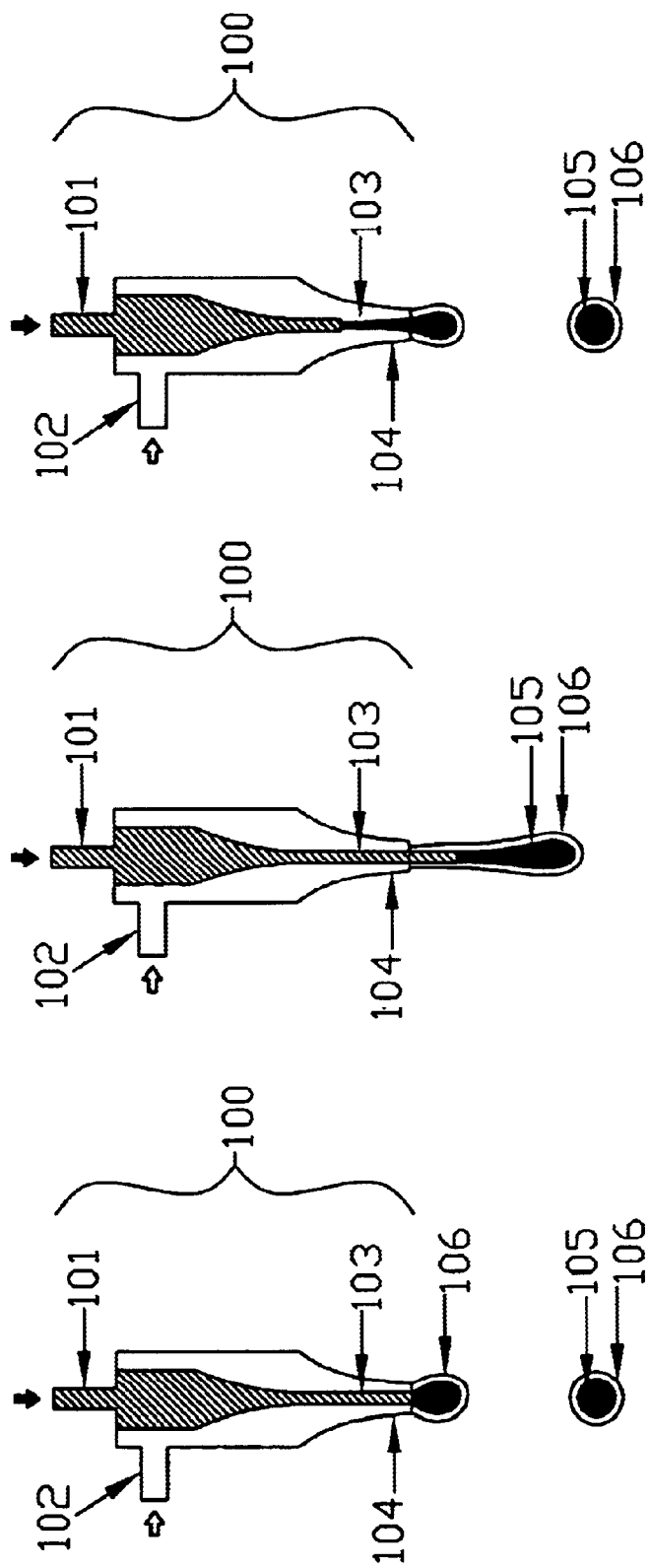
FIG. 2A: Flush nozzle design.
FIG. 2B: Protruding nozzle design.
FIG. 2C: Recessed nozzle design.

Concentric nozzle systems 100 for use in this invention can be constructed from a variety of materials, including glass, ceramic, plastic, and metal. Glass nozzles have the advantage that they are transparent and this allows easy visual inspection of the contents and condition of the nozzle. Metal (aluminum, brass, stainless steel, etc.) nozzles, however, are generally more rugged and easier to fabricate. Three examples of nozzle geometries are depicted in FIGS. 2A, 2B, and 2C. FIG. 2A depicts the end of inner nozzle 103 containing the core material 105 flush with the end of the outer nozzle 104, which contains the coating material 106. Coating material enters the nozzle 100 through inlet 102; core material enters nozzle 100 through inlet 101. FIG. 2B depicts the inner nozzle 103 protruding from the outer nozzle 104. FIG. 2C depicts the inner nozzle 103 recessed from the outer nozzle 104. In the flush and protruding nozzle examples it is necessary that the diameter of the outer nozzle be greater than that of the inner nozzle. For FIG. 2C, it is possible that the inner core nozzle 103 can have a diameter larger than that of the outer coating nozzle 104. Depending on the variation of nozzle used, whether flush, protruding, or recessed, the inner core nozzle 103 diameter can range between 0.1 mm and 5.0 mm, while the outer core nozzle 104 diameter can range between 0.1 mm and 5.0 mm.

Figure 3:
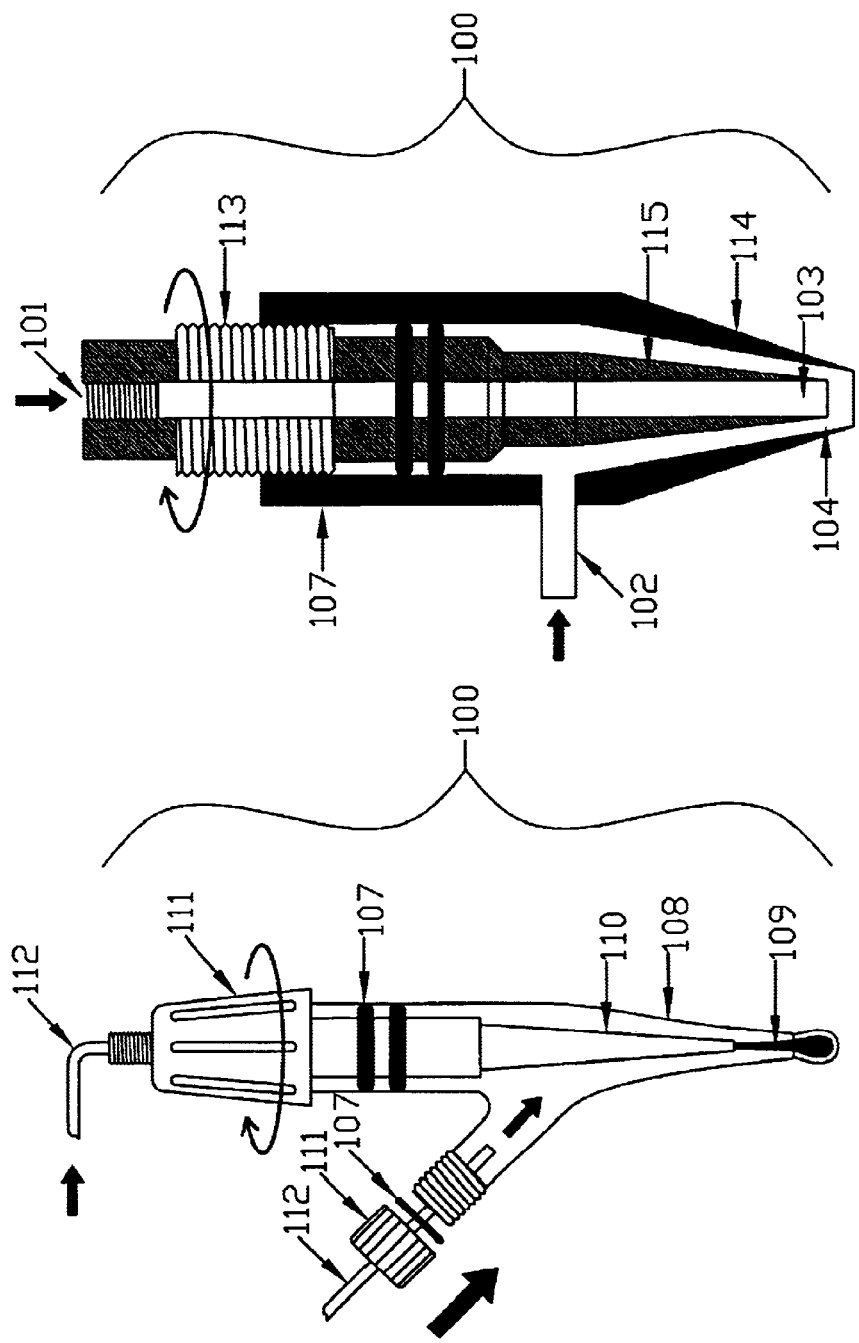
FIG. 3A: Glass adjustable nozzle design.
FIG. 3B: Metal adjustable nozzle design.

An example of one convenient adjustable nozzle design is depicted in FIG. 3A. FIG. 3A is a recessed nozzle fabricated from a glass/PTFE rotoflow stopcock 110 such as is commonly used on scientific equipment and laboratory glassware. The glass outer shell 108 can be made of borosilicate glass with an outer diameter ranging between 6 mm to 20 mm, but preferably about 10 mm to 15 mm and an inner diameter ranging between 4 mm to 18 mm, but preferably about 8 mm to 12 mm. The inner tubing 109 can be made of stainless steel with an inner diameter ranging between 0.1 mm to 5 mm, but preferably about 0.8 mm and an outer diameter ranging between 0.4 mm to 7 mm, but preferably about 1.5 mm. The inner tubing 109 can be tapered on one end and inserted through the center of the stopcock plug 110, which is preferably made of Teflon. The glass outer shell 108 is tapered so that the flow of the coating material 106 (as shown in FIG. 2A) can be adjusted by rotating the PTFE plug 110 up or down. The use of a glass outer shell 108 allows the user to visually check the annular gap between the inner and outer components, in order to ensure that they are concentric and the gap is unobstructed. Screw-type chromatography fittings 111 and/or O-ring type compression fittings 107 can be used to secure the connecting tubing 112 to the nozzle assembly 100. The glass outer shell 108 may be covered with a suitable material (tape, foil, or paint) in order to shield the light-sensitive coating material 106 (as shown in FIG. 2A). FIG. 3B depicts a similar nozzle as shown in FIG. 3A, except that the nozzle in FIG. 3B is a metal nozzle based on a needle valve with a screw type fitting 113 to accurately regulate the flow of liquid. The metal outer shell 114 can be made from commonly available metals such as stainless steels, brass alloys, or aluminum alloys, and in any combination of these metals.

The choice of orifice size will vary depending on the particular materials and application which are selected. In general, orifice diameters in the range of approximately 0.005" to 0.100" are most useful. The use of larger diameter nozzles will generally result in the formation of larger hydrocapsules. The use of larger diameter nozzles also allows fluids of higher viscosity to be pumped using lower pressures. Nozzle assemblies which contain more than one set of concentric bores are also useful, particularly for high output applications. The use of multiple nozzles simultaneously is also possible.

After emergence from the concentric nozzle 100 (FIG. 1), the fluids enter into a reaction zone, which comprises the activation column 200 and the activation chamber 300 as shown in FIG. 1. Inside this reaction zone, energy input of some type is supplied in order to accomplish polymerization, solidification, and/or crosslinking of the shell material. Depending on the characteristics of the fluids used, and the choice of operational parameters, the fluids exiting from the bottom of the nozzle assembly 100 emerge as either a biliquid column or a series of concentric liquid droplets. In general, fast fluid flow rates will result in a biliquid stream; whereas, low flow rates will generate discrete droplets. The size of the concentric droplets will generally be larger when the system is run in the discrete droplet mode. Under the influence of gravity, the biliquid stream will break-up into multiple smaller discrete droplets. This effluent can enter into a fluid which provides some bouyancy, or it can be simply allowed to free-fall (either in vacuum, in air, or in another type of reactive or non-reactive gas). The concentric nozzles 100 can be submerged directly in the suspending fluid, or they can be maintained at a certain distance above the fluid in which case the droplets will fall until they eventually hit the liquid surface, and sink. It is also possible to utilize a moving stream of gas (essentially an "air cushion") in order to suspend the droplets or provide some degree of bouyancy, or to accelerate breakup of the biliquid stream into discrete droplets. The main purpose of the suspending medium (liquid or gas phase) is to slow the gravitational descent of the droplets, thus optimizing their residence time inside the reaction zone. Note that in the case where the extruded concentric droplets have a density less than that of the suspending fluid, they can be introduced at the bottom of the suspending fluid and then allowed to rise. The suspending medium can also be utilized as an aid in the preparation of larger microcapsules which would otherwise break or deform due to gravitational and/or shearing effects. The residence time of the concentric spherical biliquid microcapsules can thus be adjusted in order to allow the polymerization, solidification, and/or crosslinking reactions to proceed to substantial completion.

The use of a liquid suspending bath is a preferred mode of this invention. Naturally, the relative densities of the concentric droplets and the suspending fluid 214 will determine the rate of fall (or rise). The system is arranged so that the droplets eventually enter into a reaction zone where they are solidified. The size of this reaction zone, the rate of migration of the falling droplets, and the kinetic parameters of the polymerization reaction will determine the necessary residence time inside the reaction zone. One requirement for the suspending medium chosen is that it must be compatible with (i.e. not dissolve or otherwise unfavorably change) the shell composition. The most useful liquid suspending medium will generally be a water-based composition. This is naturally apparent, given the fact that the shell materials have already been chosen to be compatible and immiscible with aqueous liquid cores. However, where a substantially non-aqueous liquid is encapsulated, it may be necessary to include a hydrophilic component in the encapsulant, and the suspending solution may preferably be non-aqueous.

The suspending fluid 214 may be pure water, or it may contain modifiers to adjust parameters such as density, surface tension, or energy absorption. Dissolved compounds such as salts or water-miscible organic liquids such as alcohols or acetone are useful to increase or decrease the density of the suspending medium. Addition of surfactants to the suspending fluid can serve to influence droplet size, and stabilize the falling droplets. Additionally, surfactants can reduce the surface tension of the suspending fluid. This is particularly useful when the concentric nozzles 100 are not submerged into the suspending fluid 214, and the falling droplets must penetrate the fluid surface. The suspending fluid 214 does not need to be homogeneous. The use of a density gradient has been found to have utility, as has the use of a gas/liquid mixture. In the latter case, a stream of inert gas bubbles is introduced at the bottom of the fluid column. These bubbles rise and flow counter-current to the falling droplets and thus provide some degree of bouyancy and mixing. When this approach is utilized with a high ratio of small bubbles, the lower density of the resulting foam can actually be utilized to encourage sinking of the droplets. Directional flow of the suspending fluid 214 also has some utility. Thus, the fluid medium can be pumped as a whole to carry the suspended microcapsules, or discrete jets at strategic locations can be used to "steer" the droplets. These flows are also useful for clearing the reaction zone of unwanted residues and debris, and to eliminate undesirable temperature fluctuations and convection currents. Flows of liquid or gas, as well as other stirring techniques (such as mechanical) can be useful for providing the shearing force necessary for the breakup of larger droplets into smaller ones.

Note also that although the technique is described as utilizing a concentric biliquid stream to produce concentric biliquid spheres, it is possible to utilize alternative means to achieve this as well. For instance, two individual liquid streams of mutually immiscible liquids can be caused to intersect, thus producing concentric liquid droplets. Similarly, a suspension of aqueous liquid in a reactive polymerizable liquid can be used to achieve the same goal. Useful combinations of all the techniques described herein are foreseeable, and will depend on the requirements for a given application.

Figure 4:
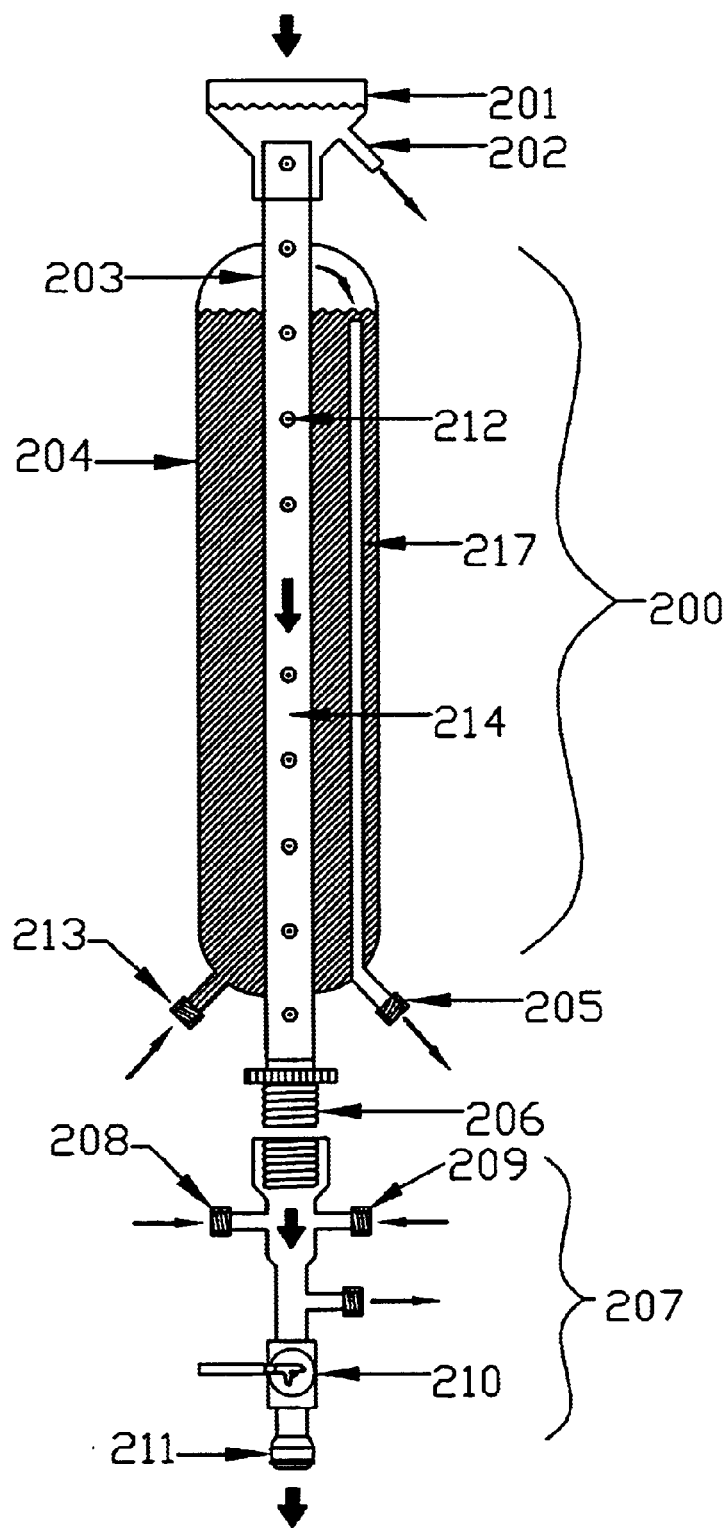
FIG. 4: Sketch of activation column and lower adaptor.

Naturally, the suspending fluid must be held in some type of container. The size and shape of the container needed will depend on the particular materials being utilized, as well as the desired throughput. FIG. 4 depicts the activation column 200. The container 203 can be a small, laboratory-scale (<0.1L) container, but can range up to an industrial scale (>100L) production. The length of the activation column 200 can vary between 30 cm to 1000 cm. The inner diameter of the container 203 can range between 1 cm to 30 cm and the outer diameter of the container 203 can range between 2 cm to 60 cm. Engineering concepts familiar to one skilled in the art will be recognized as being important to this goal. Non-linear scaling of operational parameters such as thermodynamic heat-transfer, and materials selection are examples of factors having importance in this regard.

Tubular-shaped containers are particularly useful for containing the suspending fluid, and as vessels for the polymerization, hardening and/or crosslinking reactions of the hydrocapsule 212 shells. Glass containers have a particular advantage that they are chemically inert, relatively inexpensive to fabricate, and are optically transparent. The latter property makes it easy to visually observe the processes occurring inside the activation column 200. The use of a transparent column also facilitates the use of light (visible or ultra-violet) as a curing mechanism for polymerization, hardening and/or crosslinking. A preferred mode of this invention is the use of ultra-violet (UV) light to catalyze, initiate, and/or promote the curing and free radical chain polymerization of vinyl monomers, oligomers, and crosslinking agents, which comprise the principal components of the shell formulations of this invention. Quartz glass has UV transparency which far exceeds that of borosilicate glass (which is the material generally used for most common laboratory glassware). Thus, most of the developmental experiments of this invention have been carried out using an activation column 200 fabricated of pure quartz. This ensures that the maximum possible UV light efficiency is achieved at the point of reaction inside the column. Borosilicate glass columns can be utilized successfully in applications where sufficient radiation can be achieved without its use. For situations where this invention is practiced utilizing other curing mechanisms such as thermal, microwave, electron beam, or visible light, quartz devices would not be expected to provide the same practical benefits. Metal, plastic, ceramic, or borosilicate glass columns would be expected to be satisfactory for such applications. Note that it is of course possible to put transparent (quartz or other materials) windows at appropriate places in the column in order to allow transmission of curing radiation, or to serve as observation ports. These observation ports can be viewed by a person directly, or connected to an automated remote monitoring device such as a video camera, fiber optic, particle counter, or other type of sensor.

It is very useful to incorporate some form of temperature control into the activation column 200. The container 203 in FIG. 4 is constructed with a water jacket 204 to allow transfer of heat into and out of the reaction zone. The entire jacketed column can be constructed of quartz, which permits the incident UV light to penetrate the entire apparatus without attenuation. Note that distilled water can be utilized as the heat transfer agent inside the chiller/heater unit 700 (shown in FIG. 1). Water is used because it is UV transparent. Distilled or deionized water can be used in order to prevent mineral deposits from forming which could block some of the incident radiation. The water jacket 204 is connected to the thermostated circulating column coolant pump 701 (FIG. 1), such as is commonly used for known laboratory and industrial applications. The flow rate and heating or cooling capacity must be sufficient to maintain the desired temperature inside the activation column 200. The type of UV lamp commonly utilized for polymerization and curing applications also emits a large amount of visible and infrared (IR) radiation, and this causes the reactor to become quite hot. The vinyl polymerization which occurs as the shell material cures also generates a lot of heat which must be dissipated. Efficient cooling is necessary to keep the system within desired operational parameters. Note that it is also possible to utilize a similar design which employs multiple temperature zones in order to control reaction rates, or other processes. Of course, other forms of temperature regulation may be employed as well. Immersion heaters and chillers can be used, as well as forced-air systems. Alternatively, the entire suspending fluid can be re-circulated through a thermostated control device. The column 203 is connected to a lower adaptor 207 at the lower end via an o-ring compression fitting 206 with screw threads. The lower adaptor 207 is preferably made of borosilicate glass and is equipped with inlet 208 for the introduction and removal of the suspending fluid 214 and inlet 209 for the introduction of inert gases for purging the system. The inner and outer diameters of inlets 208 and 209 can vary between 5 mm to 25 mm. The suspending fluid solution 214 (for example, a 0.5% solution of sodium dodecyl sulfate in distilled water) can be pumped into the bottom of the column via a laboratory tubing/roller type peristaltic pump 216 (as shown in FIG. 1). The gas inlet 209 can be equipped with a sintered glass frit to allow inert gas (nitrogen or argon) to be bubbled into the suspending fluid 214 in order to remove dissolved oxygen which could interfere with UV-curing of the shell. The suspending fluid 214 can be allowed to overflow the top of the column, and the overflowing liquid is collected in a removable spill funnel 201 equipped with an overflow drain 202. This allows fresh suspending fluid to be continuously pumped into the column during operation, in order to remove suspending fluid which in some cases can become clouded by leakage of core liquid from uncured hydrocapsules 212. The upper portion of the column which extends beyond the water jacket 204 can be covered (with paint, tape, or foil, for example) in order to prevent UV light from being emitted into the workplace. Note that the water jacket 204 on the activation column 200 is designed with both an inlet port 213 and an outlet port 205 at the lower end in order to allow unrestricted access to the upper portion of the tube. This is facilitated by using a return tube 217 inside the water jacket 204.

Once the hydrocapsules 212 have achieved sufficient mechanical strength to allow handling, and they have been cured sufficiently to prevent them from sticking together, they are generally collected in a receiver 400 (as shown in FIG. 1). It is convenient to employ some type of valve assembly, such as the cut off isolation gate valve 210, to allow the collected capsules to be recovered from the reaction column and collected without disturbing the continuing process. The receiver 400 (as shown in FIG. 1) can be connected to the lower adaptor 207 through use of a ball joint 211.

Figure 5:
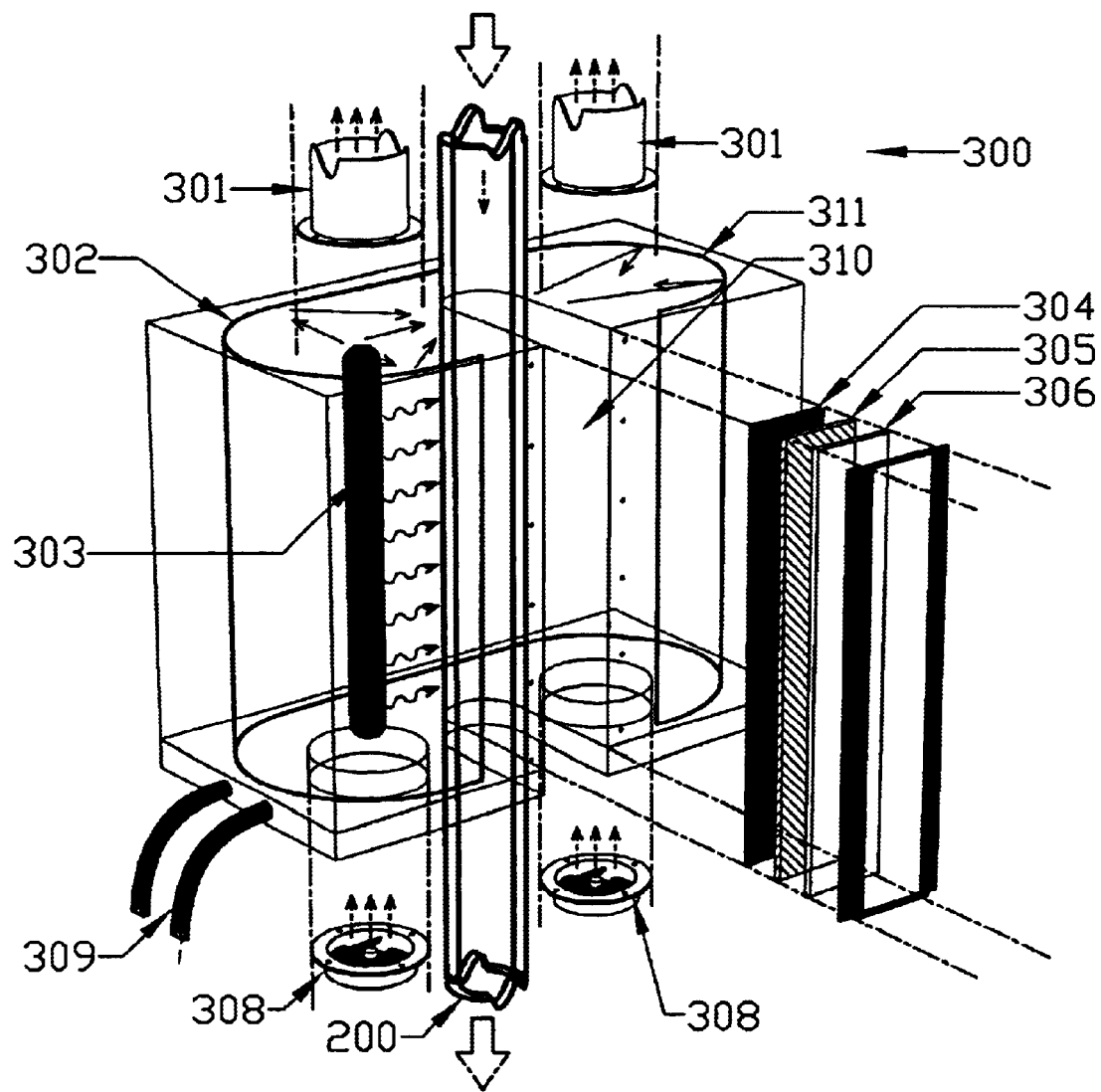
FIG. 5: Sketch of activation UV chamber.

A preferred mode of this invention is the use of ultraviolet (UV) light to catalyze, initiate, and/or promote the curing and free radical chain polymerization of vinyl monomers, oligomers, and/or crosslinking agents, which are principal components of the shell formulations of this invention. Thus, the reaction chamber must be interfaced to the energy (UV) source in some manner. FIG. 5 depicts an arrangement which was used successfully for developmental-scale research. The center of the activation column 200 is enclosed in a metal box 307 which has a slot 310 to accommodate the activation column 200. The activation column 200 thus passes through the center of the metal box 307. The metal box 307 can be made of any metal but typically aluminum or stainless steel. The length of box 307 can vary between 30 cm to 1000 cm, the width can vary between 15 cm to 100 cm, and the height of box 307 can vary between 15 cm to 100 cm. A high energy mercury vapor lamp 303 equipped with a parabolic reflector 302 can be used to supply radiant UV energy. The length of the mercury vapor lamp 303 can vary between 5 cm and 600 cm, but is preferably 25 cm long, with a power rating of 80 to 120 Watts per cm (2–3 KW total). The lamp 303, lamp housing 307, reflector 302 and power supply 800 (as shown in FIG. 1) can be purchased as a unit from Hanovia Co. (Union, N.J.). A second polished aluminum reflector 311 may be placed on the opposite side of the activation column 200 in order to maximize the intensity of incident radiation at the desired location. The activation chamber 300 is constructed such that the central axis of the activation column 200 is parallel to the UV lamp 303 and coincident with the focal point of the parabolic reflector 302, which is approximately 3 inches from the lamp. Since reaction of UV radiation with air produces ozone gas which is toxic, the activation chamber 300 is equipped with multiple exhaust fans 308 and vent ducts 301. The vent ducts 301 can be made of 3" ducting connected to a high flow blower intake. All openings in the housing are sealed with aluminum reflective tape to prevent emission of hazardous UV radiation into the workplace. The activation chamber 300 is also equipped with windows 304, 305, and 306 which comprise a 3-layer window. Window layer 304 is preferably made of ¼" thick borosilicate glass due to its extremely low coefficient of thermal expansion. The borosilicate glass serves to protect the outer layers from any thermal shock associated with the high temperatures inside the activation chamber 300. The second window layer 305 is made of red filter glass such as is commonly used in protective eye gear. The thickness of the layer 306 can range between ⅛" and ½", but is preferably ¼" thick. The outer window layer 306 is made of plexiglass, and serves as a protective layer to prevent against accidental contact of the hot inner layers by the operator. The thickness of layer 306 can range between 1/16" and 1/2", but is preferably 1/8" thick. An air gap of about 1/4" is left between the layers for cooling purposes. Electrical power is supplied to the activation chamber 300 through cords 309 running from the power supply 800 (as shown in FIG. 1).

Figure 6:
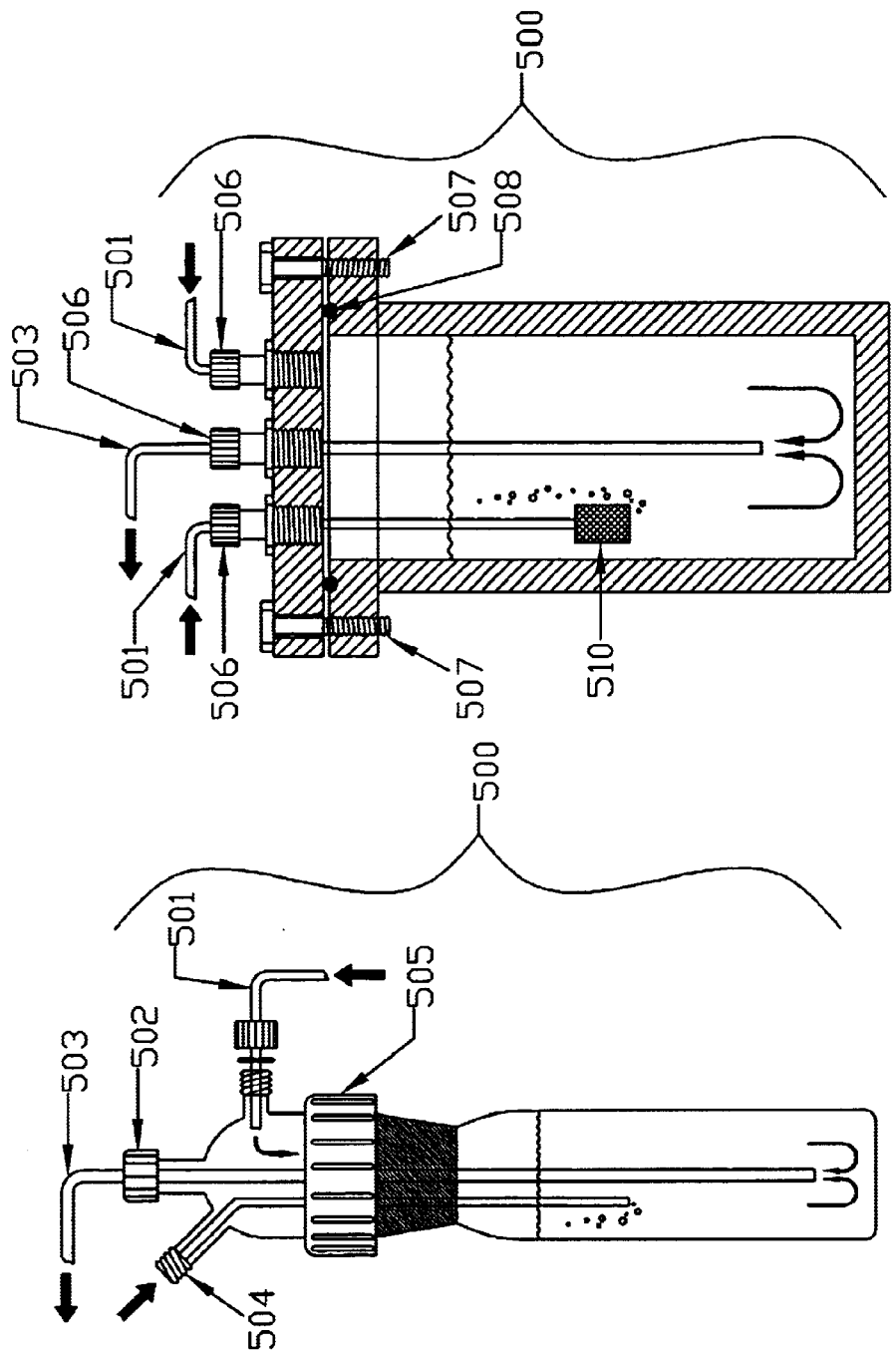
FIG. 6A: Sketch of glass reservoir.
FIG. 6B: Sketch of metal reservoir.

FIGS. 6A and 6B depicts two embodiments of the reservoirs 500 which contain the coating and core material. The size, geometry and construction of the reservoir is understood to be versatile, and will generally be determined by the specific requirements of the particular user (materials selection, production rate, chemical reactivity, etc.). For general, laboratory-scale development, reservoirs can range in size from about 50 mL to about 300 mL. A glass reservoir, as shown in FIG. 6A may be used for low to medium working pressures up to about 30 psi. Tubing 501 in FIG. 6A is used to receive pressurized gas in from the gas pressure system 600. Tubing 503 carries the material from the reservoir 500 to the nozzle system 100. Inlet port 504 can be used as an extra vent for venting or purging. Tubing 501 and tubing 503 are connected to reservoir 500 through use of removable o-ring caps with a threaded glass connector 502. The reservoir opens apart to facilitate filling with a RodaViss glass joint with a removable screw top 505. FIG. 6B depicts a metal reservoir for use in medium to high working pressures. The following metals can be used to make the reservoir, stainless steels, aluminum and brass. The metal reservoir depicted in FIG. 6B also contains tubing 501 which is to receive pressurized gas from the gas pressure system 600 in order to push material out through tubing 503 into the nozzle system 100. The metal reservoir in FIG. 6B also contains an optional purging port 510. The purging port 510 and tubing 501 and 503 are all connected to the reservoir through use of metal-tube compression fittings 506. The reservoir 500 in FIG. 6B opens to facilitate filling and can be sealed through use of o-ring grooves 508 and metal bolts 507. The need for higher working pressures would result from a need for increased throughput (or flow), as a result of using liquids with very high viscosities, or a need to push the liquids through very small orifices or long lengths of narrow-bore tubing. In some cases it may be desirable to heat the reservoirs slightly. This will lower the viscosity of the contents, allowing lower gas pressures and higher flows to be used. Preheating of the liquids can also serve to provide enhanced rates of reaction during the subsequent polymerization step. Since many of the coating materials used in this invention are sensitive to light, the glass reservoirs must also be equipped with some form of shielding. This can be in the form of a metallic coating, a suitable paint-like coating, wrapping with aluminum foil, or simply encasement in a light-proof box, for instance. It is desirable, but not strictly necessary, that the reservoirs be equipped with some type of mechanism to determine the level of fill.

Figure 7:
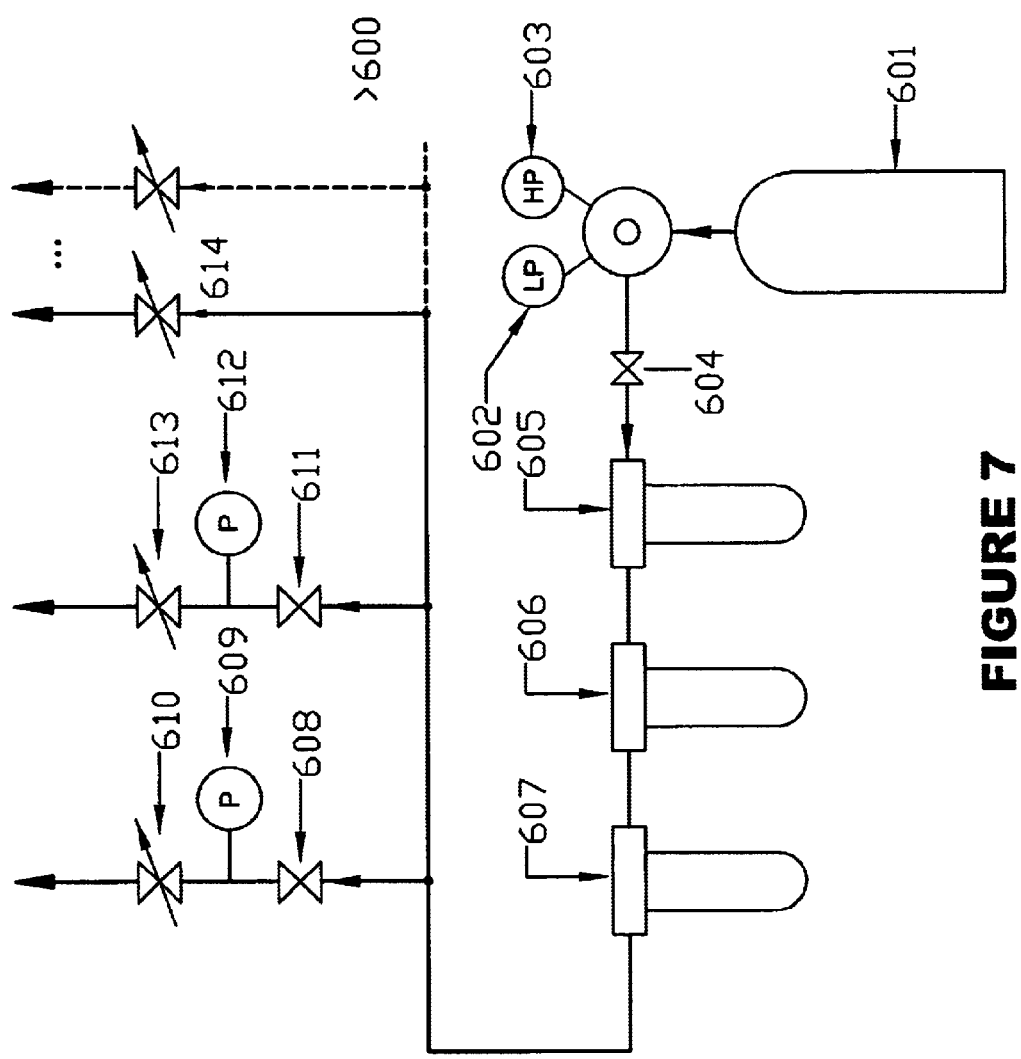
FIG. 7: Schematic of gas pressure system.

The aforementioned liquids can be forced through the concentric nozzle 100 by gas pressure. FIG. 7 depicts a gas pressure system 600 which can be used for filtration, pressure regulation and flow control of all gases used in the co-extrusion process. The gas can be of any type as long as it is not reactive to the coating and core materials. Preferably, the gas is non-toxic or inert. In the present invention, both air and argon have been used. The gas, from a high pressure tank 601 or house compressor system enters at an intermediate pressure in the range from 50 to 300 psi. The pressure tank 601 in FIG. 7 has both a low pressure gauge 602 and a high pressure gauge 603. The system has a cut-off valve 604 before the gas enters a 3-stage gas filtration system. The gas filtration system consists of three gas purification filters. Filter 605 is used to remove water; filter 606 is used to remove particulates greater than 0.1 $\mu$m and filter 607 is used to remove hydrocarbon impurities to less than 1 ppm. The gas is then channeled off into pressure regulators and flow controllers. Pressure regulator 608, pressure gauge 609 and the adjustable flow controller 610 are used to regulate and control the flow of coating material being pushed through the nozzle system 100. Pressure regulator 611, pressure gauge 612 and adjustable flow controller 613 are used to regulate and control the flow of core material being pushed through the nozzle system 100. Adjustable flow control 614 can control the use of optional moving streams of gas bubbles in the container 203 of the activation column 200. Ideally, the flow and pressure control valves should be of high quality and have excellent resolution (fine adjustment capabilities), because even the smallest changes in pressure to one of the phases can change the thickness of material that is being applied to form a coated droplet. It is to be understood that these flow control functions can be performed manually, or by an automated system with some type of sensor/feedback control mechanism.

It is also possible to utilize mechanical pumping, either instead of, or in conjunction with, the gas pressurization, in order to control the flow of the two liquid components. Various types of pumps are suitable for this purpose. Syringe pumps offer excellent flow control with non-pulsating flow characteristics. These types of pumps are particularly well-suited for laboratory and intermediate-scale applications, and can be used with both aqueous or non-aqueous (core) and organic (coating) fluids. Peristaltic roller-type laboratory pumps are also useful for some fluids (particularly low to medium viscosity aqueous liquids). Piston-type metering pumps can also be used. For large-scale pumping, or for controlled pumping of viscous organic fluids, a gear-type metering pump is preferred. Note that it is possible to utilize one type of pump for one of the two fluids, and a different type of pump for the other, depending on the particular application. Roller and piston type pumps provide a pulsed flow profile, which can be utilized to provide flow surges which can aid in droplet formation. Pumping rate from all types of pumps can be controlled either manually, or by an automated system.

Connections between the reservoirs, pumps, concentric nozzles, and/or pressure sources can be made by suitable tubing or pipe. For low-pressure laboratory applications, flexible, non-reactive, thick-walled tubing made from polyethylene or similar materials (such as PTFE or polypropylene) is quite satisfactory. Generally, tubing with an internal diameter of 1/16 to 1/4 inch is satisfactory. The tubing should not be reactive to, or be affected by the liquids being pumped. For instance, silicone or PVC tubing are not satisfactory for pumping many organic liquids, but are satisfactory for many aqueous fluids. It is also possible to utilize metal (such as copper or stainless steel) tubing, particularly when the system is operated at high pressures. It is expected that large scale (industrial) implementation of this invention would utilize metal plumbing, such as that which is commonly used for similar industrial process applications.

Many factors will affect the flow characteristics of the fluids utilized in this invention. The viscosity of the liquids being pumped is a primary factor to be taken into consideration when calculating the relationship between applied pressure and the resulting flow rate. Liquids with higher viscosities will require higher pressures in order to achieve identical flows through a particular system. Narrower tubing and orifices, as well as longer pumping distances will naturally require higher backing pressures. This effect allows the geometry of the plumbing to be adjusted in order to control flow. For instance, it is more difficult to accurately control the flow of a low viscosity fluid through a short wide-bore tube by making small pressure adjustments than it is to control the same fluid when flowing through a long narrow-bore tube. Similarly, it is difficult to get a quick flow-change response in a long, narrow, high viscosity system, by making only a small pressure change. Temperature can also be used to raise or lower the viscosity of a fluid in order to achieve more accurate flow control.

Many of the liquid shell-forming materials which are useful in the practice of this invention can be selected from the broad class of vinyl compounds. These are compounds which contain one or more polymerizable vinyl (—CH=CH$_2$) groups. These vinyl-containing shell-forming materials may be relatively low molecular weight compounds (<200 amu) which are generally referred to as "monomers", or they may be larger molecules (>200 amu) which are generally referred to as "reactive oligomers", "macromonomers", or "prepolymers". Thousands of such compounds are known, and it will be recognized by one skilled in the art that there is a myriad of formulations which can be useful in the practice of this invention. Blends and mixtures in various proportions of all of the types of compounds discussed below can be useful in the practice of this invention. Commonly known acrylate monomers such as methyl methacrylate (MMA), acrylic acid (AA), butyl acrylate (BA), hexyl acrylate (HA), and hydroxyethyl methacrylate (HEMA), are examples of useful low molecular weight monomers. Other less common acrylic monomers like long-chain alkyl acrylates and methacrylates (such as C$_{12}$-to C$_{24}$-acrylates), tetrahydrofuranyl acrylate, or caprolactone acrylate, for instance, can be used to impart useful properties to the shell formulation. Other commonly known vinyl monomers such as vinyl chloride, styrene, vinyl acetate, or other compounds can also be used in this application. In general, any reactive polymerizable compound which can be incorporated into a liquid formulation may be utilized. Examples of low molecular weight difunctional compounds would include divinyl benzene (DVB), ethylene glycol dimethacrylate (EGDMA), trimethyloyl triacrylate, and hexane diacrylate. Many other similar compounds are also useful. The use of multifunctional (compounds which contain two or more vinyl units per molecule) will lead to the formation of crosslinked network polymers. Such polymers have desirable properties such as good mechanical strength, elasticity, toughness, and flexibility.

Representative monomers which can be employed according to this invention include but are not limited to acrylic acid, methacrylic acid, methyl acrylate, ethyl acrylate, propyl acrylate, n-butyl acrylate, pentyl acrylate, hexyl acrylate, 2-ethylhexyl acrylate, heptyl acrylate, octyl acrylate, nonyl acrylate, decyl acrylate, dodecyl acrylate, tetradecyl acrylate, hexadecyl acrylate, isopropyl acrylate, isobutyl acrylate, sec-butyl acrylate, 2-methylbutyl acrylate, 3-methylbutyl acrylate, 1-ethylpropyl acrylate, 2-methylpentyl acrylate, 2-ethylbutyl acrylate, 1,3-dimethylbutyl acrylate, 1-methylhexyl acrylate, 2-ethylhexyl acrylate, 1-methylheptyl acrylate, 4-ethyl-1-methyloctyl acrylate, 4-ethyl-1,1-isobutyloctyl acrylate, allyl acrylate, 2-methylallyl acrylate, 1-methylallyl acrylate, 2-butenyl acrylate, 1,3-dimethyl-3-dibutenyl acrylate, 3,7-dimethyl-7-octenyl acrylate, 3,7-dimethyl-2,6-octadienyl acrylate, 3,7-dimethyl-6-octenyl acrylate, tert-butyl acrylate. Representative ester monomers of methacrylic acid which can be used include methyl methacrylate, ethyl methacrylate, n-propyl methacrylate, isopropyl methacrylate, n-butyl methacrylate, isobutyl methacrylate, sec-butyl methacrylate, tert-butyl methacrylate, n-hexyl methacrylate, n-octyl methacrylate, isooctyl methacrylate, decyl methacrylate, n-dodecyl methacrylate, n-tetradecyl methacrylate, n-hexadecyl methacrylate, 2-ethylhexyl methacrylate, allyl methacrylate, oleyl methacrylate, 2-propynyl methacrylate, and the like. The above monomers may be employed separately or in various mixtures according to this invention.

The utilization of reactive prepolymers (which may be monofunctional or multifunctional) allows a wide range of materials properties to be achieved using this invention. In general, reactive prepolymers have higher viscosities than low molecular weight monomers. This property is very useful in that it allows the viscosity of the shell-forming liquid to be controlled. Useful classes of reactive prepolymer materials include polyurethane acrylates, unsaturated polyesters, polyether acrylates, functionalized epoxides, and functionalized silicones (among others). These reactive prepolymers may be monofunctional, or they may be multifunctional.

The polymerization of vinyl-containing compounds is not the only polymerization mechanism which is useful in the practice of this invention. For instance, the ring-opening polymerization of monomers such as ethylene oxide, caprolactone, tetramethyl disiloxane, and similar compounds can also be utilized to form a polymer shell surrounding an aqueous core. Likewise, metathesis polymerization of olefins induced by transition metal catalysts may also be employed for shell formation.

Non-reactive components may also be incorporated into the shell-forming formulations. These types of compounds do not react with the vinyl groups present in the formulation, but instead are added to impart some type of desirable property to either the shell-forming liquid (such as viscosity control) or to the final shell polymer (such as a plasticizing effect). Such compounds may be of any molecular weight. The use of nonreactive polymers in the shell formulation will result in a polymer blend or interpenetrating network after the reactive vinyl components of the formulation have undergone polymerization. Volatile components can also be added in order to facilitate processing, or to modify the properties of the final shell materials. Many types of plasticizers are commonly used in the polymer industry, and can also be used in conjunction with this invention. Examples would include phthalates, adipates, and ureas. Other types of commonly used polymer additives such as chain transfer agents, antioxidants, anti-static compounds, UV stabilizers, dyes, and fillers can also be incorporated into the shell-forming fluids of this invention. Note that it is also possible to incorporate compounds which are not generally liquids at room temperature. A solid polymer dissolved in an appropriate liquid monomer will give a liquid solution which can be used as a shell-forming fluid. Additionally, it is possible to utilize a suspension of solid particulates in a reactive liquid matrix as the shell-forming liquid. These particles will then be incorporated into the shell material. Such particles may be used as fillers to impart desirable characteristics, such as mechanical strength, or controlled density to the cured shell. These filler particles may be metals, microcapsules or microspheres, salts, polymers, ceramics, or organic solids. The use of fillers in polymer formulations is well known in the art. Of course it is necessary that the particle size of the filler particles be small enough to avoid clogging of the various components of the apparatus. This may be accomplished by filtration of the shell-forming fluid prior to use.

The use of silicone-based UV-curable elastomers such as those available from Loctite Corporation as shell-forming components is one example of how particularly useful shell properties can be obtained. Silicone formulations such as these result in biocompatible capsules having favorable mechanical characteristics, environmentally benign properties, and dessication resistance far superior to hydrogel-based polymers such as alginate or gelatin (>100×). Silicone polymers are commonly known to have, by-far, the highest oxygen permeability of any class of synthetic polymer (Comyn 1985, Arkles 1983, and Elias 1984). The oxygen permeability of silicone is 100 times that of polyethylene. This makes it particularly suited for applications such as gas-exchange membranes in heart-lung machines (Arkles, 1983). A myriad of formulations is possible using reactive silicones blended with selected acrylic and urethane resins. Properties such as shell thickness, softness, flexibility, and permeability can be further controlled via the addition of various plasticizers and modifiers, or by adjusting the degree of cross-linking. Hydrophobicity of the membrane plays a key role in determining loss of water from the hydrocapsule. Incorporation of monomers such as octyl acrylate and hydroxyethyl acrylate will cause the shell to become more hydrophobic or hydrophillic, respectively. Films of polymers such as poly(vinyl chloride) or poly(ethylene terephthalate) have very low oxygen permeabilities (Comyn, 1985 and Elias, 1984). Appropriate modification of the shell forming solution also facilitates encapsulation of liquid cores with little or no aqueous content.

The preceding paragraphs illustrate the types of reactive vinyl compounds and additives which can be blended for use as shell-forming materials in the practice of this invention. These types of formulations are well known, and can be used in numerous other traditional polymer processes such as coatings and adhesives. The particular combination of reactants and modifiers selected for a given application will determine the properties of the resulting polymer. The same holds true for utilization of these same formulations in the current invention.

It is generally desirable to utilize shell precursor and core liquids which have nearly equal specific gravities in order to produce hydrocapsules which are perfectly concentric. It is also possible; however, to intentionally mismatch the densities of these liquids in order to prepare lopsided capsules. It has been found that these lopsided capsules have utility in that they will generally present a shell membrane which has an extremely thin wall thickness on one side. This allows the capsules to have an area which is, for instance, easily penetrable by a feeding insect, while also having the high mechanical strength associated with thick-walled microcapsules.

Polymerization of vinyl monomers can be effected by a variety of techniques. The most common and useful method is via free-radical chain polymerization. There are a number of ways to initiate the free radical polymerization of vinyl monomers. The most common involves the use of a free radical generating chemical known as an "initiator". Two of the most commonly used types of initiators are thermal initiators (generally peroxides or azo compounds), and photoinitiators. Thermal initiators rely on the input of heat in order to initiate polymerization, while photoinitiators rely on the input of light. Both classes of initiators can be used in the practice of this invention. If thermal initiators (such as AIBN, benzoyl peroxide, or cumyl peroxide) are used, then the reaction chamber will be heated to a specific temperature which is appropriate for the chosen thermal initiator (as discussed above). Polymerization by the use of photoinitiators is generally faster than by thermal methods, and thus is the preferred technique for use in this invention. This is mainly due to the very high polymerization rates which can be obtained by this method. In general, complete curing of acrylate formulations can be accomplished in a few seconds using suitable UV photoinitiators. Most of the examples given herein pertain to the free-radical initiated polymerization of shell precursors. Other suitable polymerization methods would include: cationic polymerization, anionic polymerization, coordination polymerization, metathesis polymerization, and condensation polymerization.

Photoinitiators rely on the absorbance of light in order to produce free radicals which then initiate the polymerization of the reactive vinyl groups present in the shell formulations. Many photoinitiators are sensitive to light in the UV range, and thus the use of UV light for the hardening of the biliquid shells in this invention is a preferred method. Photoinitiators which are activated by visible light are also useful. Suitable photoinitiators include benzophenones, benzoin ethers, camphorquinones, and acyl phosphine oxides, among others. In general, the concentration of photoinitiator used in the shell-forming liquids will be on the order of 0.1 to 5% by weight. Higher concentrations will generally give faster curing reactions, as will the use of higher light intensities. The use of co-initiators or synergists (compounds which enhance the efficiency of photopolymerization), such as reactive amines is also a useful variation of this invention. Polymerization techniques other than UV and visible irradiation can also be employed in this invention. For instance, it is well known that polymerization, curing, and crosslinking of polymers can be accomplished via the use of heat, electron beam irradiation, gamma irradiation, or other methods.

This invention relates to the encapsulation of liquids. The specific liquid which comprises the core of a particular hydrocapsule will depend on the intended application. In order to optimize both the production of the hydrocapsules, and the properties of the final product, it is desirable to control the properties of the liquid to be encapsulated. Factors such as surface tension, viscosity, density, and ionic strength can be modified by a variety of methods. For instance, density can be increased by addition of salts or other compounds. Viscosity can be adjusted by adding appropriate agents or thickeners. As with the shell-forming liquids, it is important that the particle size of any solid components be small enough to prevent clogging of the various instrumental components.

Liquids and other compositions which are suitable for encapsulation by this method include: foodstuffs, pharmaceuticals, cosmetics, detergents, reagents, pesticides, industrial chemicals, dyes, inks, paints, nutrients, flavorings, blood, fragrances, pure water, microbes, enzymes, catalysts, oils, alcohols and other substances. There are many potential uses for various encapsulated microbial agents. Some applications of such systems are discussed below. Note that it is even possible to encapsulate suspensions of other microcapsules or microspheres, thus producing capsules within capsules.

In view of the disclosure provided herein, those skilled in the art will appreciate that this invention pertains to a method of encapsulating discrete small volumes of liquid. By "liquid", is meant any solution, fluid, slurry, paste, suspension, or similar formulation which contains a composition of matter that falls within a continuum between liquids that are completely aqueous (100 percent water by mass) and liquids that are completely non-aqueous (0 percent water by mass). By "discrete small volumes" is meant individual drops, droplets, portions, or aliquots which have approximate volumes of between $1\times10^{-9}$ and $1\times10^{-3}$ liters. By "encapsulating" is meant the process of containing a liquid droplet within a capsule, membrane, shell, coating, skin, or similar covering. The method involves generating a continuous coating or layer of a polymerizable liquid surrounding discrete small volumes of a liquid. The "polymerizable liquid" is any liquid which may be induced to polymerize and/or crosslink under defined conditions, and which is substantially immiscible with the core liquid composition. Various forms of such liquids and induction methods have been disclosed herein and are known in the art. The polymerization and/or crosslinking of the polymerizable liquid generally results in an irreversible change of the liquid into a solid material. This solid material ultimately becomes the capsule, membrane, shell, coating or similar covering which surrounds the discrete small volume of a core liquid. By "substantially immiscible with liquid" is meant that the polymerizable liquid and the core liquid do not intermingle or form a totally homogenous mixture. For example, as is known, oil and water are immiscible, however, generally, oil is not polymerizable, and would not be adequate as an encapsulant according to this invention. Polymerization of the polymerizable liquid may be induced by any known means, including the use of energy either alone or in combination with polymerization initiators, photosensitive or thermosensitive polymerization initiators, chemical initiators and the like. As a result of the polymerization, a capsule or microcapsule is formed which is composed of a shell, membrane, or solid coating which surrounds a discrete small volume of a core liquid.

Having generally described the invention, and the preferred embodiments thereof, the following examples are provided to extend the written description of the invention and to exemplify the best mode of carrying out this invention. However, it will be appreciated that the scope of this invention should not be considered to be limited to the specifics of the examples, which are provided merely for illustrative purposes. Examples 1 and 2 demonstrate the use of this invention to encapsulate artificial diet formulations for the mass-rearing of beneficial insects. Example 3 demonstrates the use of this invention to prepare relatively large hydrocapsules containing colored water. Example 4 demonstrates the use of this invention to encapsulate entomopathogenic nematodes for use as pest control agents. Example 5 demonstrates the use of this invention for the encapsulation of an entomopathogenic bacteria for use as a pesticide. Example 6 demonstrates the formation of a hydrocapsule with a pH-sensitive shell. Example 7 demonstrates the use of this invention to encapsulate an oil-based mixture. Example 8 demonstrates the use of this invention for the encapsulation of substantially pure ethylene glycol.

EXAMPLE 1

This example demonstrates the preparation of hydrocapsules containing an aqueous-based liquid artificial diet useful for the mass-rearing of beneficial insects. The diet used in this example is an aqueous suspension of nutrients including protein, carbohydrate, lipid, and minerals. The preparation of this diet is described in detail in U.S. Pat. No. 5,799,607 (Greany et al., Sep. 1, 1998). The diet was filtered by vacuum through a 300 micron nylon mesh, and then sparged with argon gas. The specific gravity of the diet was measured and found to be approximately 1.04 g/cc. This diet was then placed in a glass reservoir similar to that pictured in FIG. 6A. A shell precursor solution was prepared by mixing a commercial aliphatic polyurethane acrylate composition (10 parts, catalog #: CN965-A80, Sartomer Company, Inc.), a mixture of monofunctional acrylate monomers (15 parts, 50/50 caprolactone acrylate and tridecyl acrylate) ), a low viscosity aliphatic diacrylate oligomer (5 parts, catalog#: CN132, Sartomer Company, Inc.), a dialkyl phthalate plasticizer (10 parts, dioctyl phthalate), and a photoinitiator (1 part, benzoin isobutyl ether). The specific gravity of this mixture was measured and found to be approximately 1.04 g/cc. The mixture was then placed into a glass reservoir similar to that pictured in FIG. 6A, heated to approximately 60° C., sparged with argon gas, and then cooled. The entire reservoir was covered with aluminum foil in order to shield the solution from ambient light. A quartz polymerization column such as that shown in FIG. 4 was filled with a solution of 0.5 wt % sodium dodecyl sulfate (SDS) in deionized water. The SDS solution was sparged with argon gas. Cooling water was pumped through the water jacket of the quartz column in order to maintain the internal temperature at approximately 30° C. The reservoirs were connected by ⅛" diameter polyethylene tubing to a glass concentric nozzle such as that pictured in FIG. 3A. The i.d. of the internal stainless steel orifice was approximately 0.020", while the i.d. of the outer (lower) orifice was approximately 0.025". The glass portion of the nozzle was covered with black electrical tape in order to prevent exposure of the contents to stray light. The tip of the concentric nozzle was positioned approximately 1" above the surface of the SDS solution. The two reservoirs were connected via ⅛" polyethylene tubing to the gas control system (FIG. 7) which was also connected to a supply of dry argon at 30 psi. The quartz polymerization column was illuminated by a 2000 watt Hanovia mercury vapor UV lamp enclosed in a housing as depicted in FIG. 5. The overall experimental setup is diagramed in FIG. 1. The argon pressure to each of the two glass reservoirs was adjusted to be approximately 10 psi. This allowed both solutions to flow from the reservoirs to the concentric nozzle assembly. Concentric liquid droplets composed of artificial diet surrounded by liquid shell precursor were allowed to drop onto the surface of the SDS solution. These droplets then sank into the SDS solution, and descended at a rate of approximately 1 inch/second, while they were illuminated with UV light. Polymerization of the shell occurred as evidenced by a slight downward acceleration of the microcapsules due to the density increase of the shell which accompanies polymerization. The size of the droplets and the ratio of the dimensions of the inner and outer regions could easily be controlled by adjusting the relative flow rates of the two solutions. If the relative flow of diet exceeded the flow of shell precursor by too much, then only solid beads of precursor were observed. This was accompanied by a noticeable clouding of the suspending medium (SDS solution). When this occurred, the flow rates were corrected to resume capsule formation, and the suspending medium was cleared by pumping fresh medium into the lower end of the column and allowing the clouded solution to overflow from the top of the column. In general it was possible to maintain capsule formation with an encapsulation efficiency of greater than 95%. Microcapsule production was carried out at an approximate production rate of 1 to 5 capsules per second. The falling polymerized microcapsules were collected in a 250 mL flask attached to the lower end of the column. At the end of the encapsulation experiment the capsules were collected on a steel strainer and rinsed with tap water. Solid beads of polymer were separated from filled microcapsules by allowing the product to distribute itself in a salt/water solution having a density appropriate to allow solid polymer beads to sink, while allowing filled microcapsules to float. The finished microcapsules were then washed several times with distilled water and allowed to dry in air for several hours. The finished microcapsules had diameters of approximately 1 to 4 mm, and were round. Shell thicknesses were determined either by visible or scanning electron microscopy, and were found to range from approximately 10 to 100 microns. It was found that these microcapsules could be stored in sealed refrigerated vessels for an extended period of time, with years of stability anticipated. They were also unaffected by freezing, or by sterilization using electron beam irradiation. These artificial diet containing microcapsules exhibit the appearance of actual insect eggs. Successful attempts were made to feed a variety of insects including ants, cockroaches, predatory mites, and lady beetles.

EXAMPLE 2

In this example a liquid insect diet having a proprietary composition was obtained from a manufacturer of beneficial insects. A shell precursor solution was prepared by mixing (as in Example 1) a commercial aliphatic polyurethane acrylate composition (60 parts), a mixture of monofunctional acrylate monomers (81 parts), a liquid diacrylate monomer (10 parts of 1,6 hexanediol diacrylate), a dialkyl phthalate plasticizer (40 parts), and a photoinitiator (4 parts). This solution was found to have a density of approximately 1.02 g/cc. The i.d. of the outer (lower) glass orifice was approximately 0.015". The encapsulation was performed in a fashion substantially similar to that outlined in Example 1 (above), except that the concentric nozzle was submerged into the suspending fluid (SDS solution) by approximately 0.5". The viscosities of both the diet and shell formulation were less than in Example 1, and thus higher flow rates were observed when the system was operated at the same gas pressures. These high flow rates resulted in a higher rate of capsule production (approximately 10 to 100 capsules per second). The microcapsules produced were generally smaller (approximately 0.5 to 2.5 mm diameter) than those produced in Example 1, and had shells which were softer and somewhat thinner. These microcapsules were used to rear colonies of *Coleomegilla maculata* with a considerable degree of success.

EXAMPLE 3

This example demonstrates the formation of relatively large (up to 8 mm diameter) hydrocapsules containing colored water using a process and apparatus similar to that described in the preceding examples. In this experiment the core liquid was a solution (approximately 1 wt %) of dextran polymer (MW=20 million). Red food coloring was added to this solution in order to improve visibility of the contents. The shell precursor solution was a mixture of a commercial aliphatic polyurethane acrylate composition (9 parts), a mixture of monofunctional acrylate monomers (8.75 parts), a low viscosity aliphatic diacrylate oligomer (2 parts), a dialkyl phthalate plasticizer (6 parts), and a photoinitiator (0.7 parts), (specific chemicals as in Example 1). The i.d. of the outer orifice was approximately 0.050". The concentric nozzle assembly was immersed approximately 1" below the surface of the suspending medium (SDS solution). Large capsules with diameters ranging between 5 and 8 mm were obtained.

It has been determined that hydrocapsules containing insect diet formulations such as artificial insect diets or sugar solutions are attractive to scavenging insects such as fire ants and cockroaches. Wild fire ants have been observed carrying artificial insect diet-containing hydrocapsules down into their colonies. Laboratory studies using hydrocapsules containing dyed sugar solutions revealed the presence of dye in fire ant larvae. Thus, by combining toxic agents with these types of materials, an effective pest-control method results. For applications targeting such species it is not necessary that the pathogenic organism be released from the hydrocapsule, since this task is performed by the feeding insects. A variety of diet solutions and other attractants such as: sugar solutions, lipids (peanut oil, for instance), or commercially available attractants (ENTICE™) can be formulated in conjunction with encapsulated agents. Non-toxic entomopathogenic hydrocapsule baits should also be effective in stored product protection.

For more passive applications such as crop pests, or yard pests such as flea larvae, the hydrocapsule will not serve as a food source for the pest organism, and a passive release mechanisms is necessary. This means that the hydrocapsule must somehow change form, or degrade enough to allow the entrapped agents to escape after application. Of course, it is always possible to utilize other convenient environmental mechanisms to accomplish this task. For instance, "biodegradable" polymers such as polyesters, polyamides, polyethers, and derivatives of many naturally-occurring polymers like cellulose are susceptible to activity by other insects, animals, microorganisms, enzymes, solar radiation, or other environmental factors, and this can cause the capsules to break and release their contents. Release can also occur due to mechanical operations such as plowing and tilling.

It is possible; however, to design hydrocapsules which do not rely on outside factors for release, but have a built-in degradation mechanism. One such mechanism is that of "stimulated release". In this approach, a stable shell matrix having suitable long-term storage properties is equipped with some sort of chemically functionalized handle (or switch) which allows the contents to become "unlocked" via an appropriate mechanism. This can result in an actual mechanical breakdown of the shell, or softening (due to water absorption, for instance) which essentially converts the hydrophobic membrane into a soft hydrogel membrane. These swollen hydrogel shells exhibit properties similar to gelatin, and the softened networks can easily be penetrated by mobile organisms such as nematodes. This in itself provides some form of sustained-release in that not all the contained organisms will migrate at the same rate. The resulting hydrogel shell can also allow microbial growth into, and through the shell, resulting in eventual release of microorganisms such as bacteria and fungi. Such growth of pathogenic organisms in hydrogel media is analogous to microbial cultures made on agar in petri dishes. The mechanical properties of swollen hydrogel shells are much less robust than for the unhydrated hydrophobic state. As such, they are even more susceptible to release by environmental mechanisms such as those described in the previous paragraph. It has even been observed in the laboratory that some hydrogels can absorb water and swell to such a great extent that the polymer matrix ruptures spontaneously.

An example of this stimulated-release approach involves the incorporation of pH-sensitive monomers such as acrylic acid or N,N-dimethylaminoethyl methacrylate into hydrocapsule shell formulations to impart pH-sensitivity. The shells of the pH-sensitive hydrocapsules have similar physical properties to those produced using standard formulations. Until the shell is exposed to the required pH-range, no hydration and swelling occurs. Only after exposure to pH changes do the membranes convert to the hydrophillic form. The pH of the internal phase can be slightly buffered at a neutral pH in order to prevent premature swelling from the inside. Since water does not affect the unactivated (dormant) polymer, storage conditions may be dry or wet. Prior to release in the field, the membrane polymer is "activated" simply by rinsing or soaking in a dilute acid or base solution (pH 4 or 10) for a predetermined time. The capsule can then be rinsed with neutral water to halt the process after a desired degree of activation has occurred. The activated capsule shell will undergo a transformation to a hydrogel, absorb water, and become soft, thus allowing the contents to escape. This can be accelerated by soaking the capsules in water after activation, or the aqueous contents can act to hydrate the shell from inside the capsule. Hydration (release) rates can be controlled by adjusting the crosslink-density, the ratio of hydrophobic to hydrophillic co-monomers, pH differential, shell thickness, temperature, relative humidity, and strength and duration of the activation treatment.

Triggered release hydrocapsules can also be produced by incorporating polymers such as polycaprolactone, polyvinylacetate, or cellulose derivatives, which undergo hydrolytic degradation. In this manner otherwise stable hydrocapsules are treated with chemical agents (such as dilute acid, base, or enzyme solutions) prior to application. These treatments can serve to initiate degradation, and trigger conversion into a hydrogel.

EXAMPLE 4

This example demonstrates the production of hydrocapsules which contain a suspension of nematodes (*Steinernema feltiae*) in the core. The process and apparatus used was similar to that described in the preceding examples. A sample of the beneficial nematode (*Steinernema feltiae*) was obtained from a commercial supplier. These nematodes were suspended in a solution of sucrose (40 g/L) and dextran (1 wt %) in deionized water. The specific gravity of this nematode suspension was measured and found to be approximately 1.008 g/cc. A shell precursor solution was prepared by mixing a commercial aliphatic polyurethane acrylate composition (6 parts), a mixture of monofunctional acrylate monomers (11 parts), an acrylate-functionalized silicone (6 parts, catalog #DMS-U22, Gelest, Inc.; other specific chemicals as in Example 1), a dialkyl phthalate plasticizer (6 parts), and a photoinitiator (0.7 part). Capsules were produced in a manner similar to that described in Example 1. Microscopic examination of these capsules revealed that they contained living nematodes. Capsule diameters ranged from approximately 2 to 4 mm. A typical 3 mm capsule was estimated to contain approximately 100 living nematodes. These capsules were stored in a loosely-capped plastic vial in a refrigerator at approximately 5° C. After 9 months of storage it was observed that the majority of the encapsulated organisms were still alive as evidenced by their swimming motions when viewed under an optical microscope.

EXAMPLE 5

This example demonstrates the encapsulation of a commercial pesticide formulation (Thuricide$^R$ HPC) which is essentially a suspension of the entomopathogenic bacterium *Bacillus thuringiensis kurstaki* (otherwise known as "BT"). The activity of this suspension was stated to be 4,000 IU/mg. The nozzle dimensions were the same as described in Example 1, while the shell formulation was that described in Example 4. Capsules with an average diameter of approximately 3 mm were obtained. A sample of the encapsulated material was cultured on agar in a petri dish. After several days extensive colonization of the petri dish by BT was observed.

EXAMPLE 6

This example demonstrates the formation of hydrocapsules which contain colored water and that have a shell composed of a pH-sensitive polymer which undergoes a transition from hydrophobic to hydrophilic as the pH of the surrounding environment increases above 7. The core solution was essentially that described in Example 3. The i.d. of the lower (outer) nozzle was approximately 0.020". The nozzle was submerged approximately 1" below the surface of the suspending medium (0.5% SDS solution). The shell formulation consisted of a commercial aliphatic polyurethane acrylate composition (8 parts), a mixture of monofunctional acrylate monomers (8 parts), acrylic acid monomer (8 parts), acrylic acid polymer (8 parts), a dialkyl phthalate plasticizer (4 parts), and a photoinitiator (1 part); specific chemicals as in Example 1. Microcapsules with an average diameter of approximately 3 mm were obtained. When these capsules were soaked in a buffer solution of pH=10 overnight, significant swelling of the shells was observed. Some diffusion of the red dye out of the capsules was also noted.

EXAMPLE 7

This example illustrates the encapsulation of an oil-based mixture. The procedure was identical to that described in Example 2, except that a mixture of sucrose and peanut oil was used in place of the liquid insect diet. The relative amounts of oil and sucrose were adjusted to produce a slurry which had a bulk density of approximately 1.02 g/cc. The capsules which were produced were similar in appearance to those produced in Example 2.

EXAMPLE 8

This example demonstrates the encapsulation of substantially pure ethylene glycol. The method utilized is similar to that described in Example 1 except that the shell precursor material was a mixture consisting of 99 parts polyester tetraacrylate (CN 292, Sartomer, Co.), and 1 part photoinitiator (KT37, Sartomer Co.). The resulting capsules had hard shells.

The utilization of this method for the formation of liquid-core, solid-walled microcapsules has been described. It is expected and anticipated that the described technique is also suitable for the production of microcapsules containing a gel in the core. Note that the method is also capable of producing solid microspheres which do not contain a core, or in which the core does not contain a liquid. Additionally, the method is suited for the formation of multinuclear microcapsules (capsules which have multiple liquid core compartments which are separated from each other by polymer identical in composition to the shell). Such capsules are actually multiple single-core capsules fused together. For instance, modifications in the temperature, pressure, and the like may be made to achieve linkage of adjacent droplets such that upon polymerization, adjacent droplets fuse or become linked in a chain. In addition, it is expected and foreseeable that this invention could be utilized in conjunction with more than two concentric nozzles in order to produce capsules with multiple layers, shells, compartments, or coatings. Concentrically-aligned nozzles are useful in the practice of this invention; however, other nozzle arrangements can also be utilized. For instance, capsules can be manufactured using off-centered, or multiple inner nozzles.

From the foregoing, it will be seen that this invention is one well adapted to attain all of the ends and objects herein above set forth, together with other advantages which would be suggested to those skilled in the art based on the present disclosure and which are inherent to the process disclosed herein. It will be understood that certain features and subcombinations are of utility and may be employed without reference to other features and subcombinations. This is contemplated by, and is within the scope of the claims. As many possible embodiments may be made of the invention without departing from the scope thereof, it is to be understood that all matter herein set forth or shown in the accompanying drawings is to be interpreted as illustrative, and not in a limiting sense.

References

US Registered Trademarks (1)

Pending trademark: "HYDROCAPSULE"™ Int. Class: 005 Ser. No.: 75/797432 Filing Date: Sep. 13, 1999 Law Office: 105

U.S. Patent Documents (22)

U.S. Pat. No. 2,275,154 Merrill et al. Mar. 3, 1942
U.S. Pat. No. 2,766,478 Raley et a. Oct. 16, 1956
U.S. Pat. No. 2,799,897 Jansen et al. Jul. 23, 1957
U.S. Pat. No. 2,911,672 van Erven Dorens Nov. 10, 1959
U.S. Pat. No. 3,015128 Somerville Jan. 2, 1962
U.S. Pat. No. 3,310,612 Somerville Mar. 21, 1967
U.S. Pat. No. 3,389,194 Somerville Jun. 18, 1968
U.S. Pat. No. 3,423,489 Arens et al. Jan. 21, 1969
U.S. Pat. No. 3,779,942 Bolles Dec. 18, 1973
U.S. Pat. No. 4,096,944 Simpson Jun. 27, 1978
U.S. Pat. No. 4,178,366 Bedding Dec. 11, 1979
U.S. Pat. No. 4,615,883 Nelsen et al. Oct. 7, 1986
U.S. Pat. No. 4,701,326 Nelsen et al. Oct. 20, 1987
U.S. Pat. No. 4,744,988 Brox Dec. 19, 1989
U.S. Pat. No. 4,753,799 Nelsen et al. Jun. 28, 1988
U.S. Pat. No. 4,888,140 Schlameus et al. Dec. 19, 1989
U.S. Pat. No. 4,948,586 Bohm et al. Aug. 14, 1990
U.S. Pat. No. 5,364,634 Lew Nov. 15, 1994
U.S. Pat. No. 5,389,535 Aebischer et al. Feb. 14, 1995
U.S. Pat. No. 5,401,506 Chang et al. Mar. 28, 1995
U.S. Pat. No. 5,478,508 Suzuki et al. Dec. 26, 1995
U.S. Pat. No. 5,799,607 Greany et al. Sep. 1, 1998

Other References (20)

Arkies, B. 1983. "Look what you can make out of Silicones." Chemtech. 13:p. 542–555.
Benita, S. 1996. "Microencapsulation, Methods and Industrial Applications" Marcell Dekker, Inc. NY
Cohen, A. C. 1983. "Improved method of encapsulating artificial diet for rearing predators of harmful insects." J. Econ.Ent. 76(4):p. 957–959
Comyn, J. 1985. "Introduction to Polymer Permeability and the Mathematics of Diffusion." Chp. 1 in Polymer Permeability. Elsevier Applied Science Publishers, NY.
Deasy P. B., 1985. "Microencapsulation and Related Drug Processes." Marcel Dekker, NY., Ed. J. Comyn. P.119–288.
Elias, H. G. 1984. "Macromolecules-Structure and Properties." Plenum Press, NY. Chapter 7.
Fravel, D. R., J. J. Marois, R. D. Lumbsden, and W. J. Connick, Jr. 1985. "Encapsulation of potential biocontrol agents in an alginate-clay matrix." Phytopathology. 75:p. 774–777.
Goodwin, J. T. and G. R Somerville. 1974. "Microencapsulation by physical methods." Chemtech Magazine. October p623–626

Hagen, K. S. and R. L. Tassan. 1965. "A Method of Providing Artificial Diets to Chrysopa Larvae." J. Econ. Entomol. 58(5):p. 999–1000
Hegenbart, S. 1993. "Encapsulated Ingredients Keep Problems Covered" in Food Product Design, April. 3(1):p. 28–38.
Hoffman, M. P. and A. C. Frodsham. 1993. "Natural Enemies of Vegetable Insect Pests." Cooperative Extension, Cornell University, Ithaca, N.Y. pp. 63
Kaya, H. K., C. M. Mannion, T. M. Burlando, and C. E. Nelsen. 1987. "Escape of Steinernema feltiae from Alginate Capsules Containing Tomato Seeds." J. of Nematology. 19(3):p. 287–291.
Kaya, H. C., and C. E. Nelsen. 1985. "Encapsulation of Steinernematid and Heterorhabditid Nematodes with Calcium Alginate: A New Approach for Insect Control and Other Applications." Environmental Entomology. 14:p. 572–574
Martin, P. B., R. L. Ridgway and C. E. Scheutze. 1978. "Physical and biological evaluations of an encapsulated diet for rearing Chrysopa carnea." Fla. Entomol. 61:p. 145–152
Rose, P. I. 1987. "Gelatin in Encyclopedia of Polymer Science and Engineering." John Wiley & Sons. 7:p. 488
Sanderson, G. R., V. L. Bell, and D. Ortega. 1989. "A Comparison of Gellan Gum, Agar, K-Carrageenan, and Algin." Cereal Foods Worl. 34(12):p. 993–998
Sparks, R. E. 1981. "Microencapsulation" in Encyclopedia of Chemical Technology. John Wiley & Sons, NY. Vol. 15.
Thies, C. 1994. "Microencapsulation.: Mini Answers to Major Problems." Today's Chemist. Nov. p. 40
Thies, C. 1987. "Microencapsulation" in Encyclopedia of Polymer Science and Engineering. John Wiley & Sons, NY. 9:p. 724–745.
Walker, H. L., and W. J. Connick, Jr. 1983. "Sodium alginate for production and formulation of mycoherbicides." Weed Science. 31: p.333–338
Weeden, C. R., Shelton, and M. P. Hoffman, 1996. "Biological Control: A Guide to Natural Enemies in North America" Cooperative Extension, Cornell Univ., NY.

What is claimed is:

1. A method of encapsulating a discrete small volume of a liquid or gel ranging from completely aqueous to completely non-aqueous in composition, which comprises:

(a) generating a continuous coating, or layer, of a polymerizable liquid which surrounds a discrete small volume of a liquid or gel ranging from completely aqueous to completely non-aqueous in composition, wherein said layer of polymerizable liquid is substantially immiscible with said liquid or gel ranging from completely aqueous to completely non-aqueous in composition and, (b) inducing polymerization of said polymerizable liquid; whereby a solid polymer shell, membrane, or coating is formed which surrounds said discrete small volume of a liquid or gel ranging from completely aqueous to completely non-aqueous in composition;

wherein said polymerizable liquid contains a photosensitive polymerization initiator that initiates polymerization via absorption of energy in the form of light.

2. A method of encapsulating a discrete small volume of a liquid or gel ranging from completely aqueous to completely non-aqueous in composition, which comprises:

(a) generating a continuous coating, or layer, of a polymerizable liquid which surrounds a discrete small volume of a liquid or gel ranging from completely aqueous to completely non-aqueous in composition, wherein said layer of polymerizable liquid is substantially immiscible with said liquid or gel ranging from completely aqueous to completely non-aqueous in composition and, (b) inducing polymerization of said polymerizable liquid; whereby a solid polymer shell, membrane, or coating is formed which surrounds said discrete small volume of a liquid or gel ranging from completely aqueous to completely non-aqueous in composition;

wherein said generating step is effected by causing both polymerizable liquid and said liquid or gel ranging from completely aqueous to completely non-aqueous in composition, to flow through nozzles having a predetermined geometry and arrangement.

3. The method of claim 2 wherein said polymerizable liquid contains at least one reactive chemical structure which polymerize by a mechanism selected from the group consisting of:

step-growth polymerization, addition polymerization, vinyl polymerization, free-radical polymerization, ring-opening polymerization, cationic polymerization, anionic polymerization, coordination polymerization, metathesis polymerization, and condensation polymerization.

4. The method of claim 1 wherein said polymerization is a vinyl polymerization which occurs by a free radical chain growth mechanism.

5. The method of claim 1 where said energy is in the form of light which has a wavelength between 150 and 800 nanometers.

6. The method of claim 1 wherein said polymerizable liquid contains a photosensitive polymerization initiator that initiates a free-radical vinyl polymerization via absorption of energy in the form of light having a wavelength between 150 and 800 nanometers.

7. The method of claim 1 wherein said polymerizable liquid also contains a thermal polymerization initiator which initiates free-radical vinyl polymerization via absorption of thermal energy.

8. A method of encapsulating a discrete small volume of a liquid or gel ranging from completely aqueous to completely non-aqueous in composition, which comprises:

(a) generating a continuous coating, or layer, of a polymerizable liquid which surrounds a discrete small volume of a liquid or gel ranging from completely aqueous to completely non-aqueous in composition, wherein said layer of polymerizable liquid is substantially immiscible with said liquid or gel ranging from completely aqueous to completely non-aqueous in composition and, (b) inducing polymerization of said polymerizable liquid; whereby a solid polymer shell, membrane, or coating is formed which surrounds said discrete small volume of a liquid or gel ranging from completely aqueous to completely non-aqueous in composition;

wherein said polymerizable liquid further comprises a thermal polymerization initiator which initiates free-radical vinyl polymerization via absorption of thermal energy.

9. The method of claim 8 wherein said reactive chemical structures are selected from the group consisting of acrylic or methacrylic acids; and monomeric, dimeric, or polymeric esters of acrylic or methacrylic acids.

10. The method of claim 1 wherein said liquid or gel ranging from completely aqueous to completely non-aqueous in composition, contains between 0% and 100% water by mass.

11. The method of claim 1 wherein said a liquid or gel ranging from completely aqueous to completely non-aqueous in composition contains between 90% and 100% water by mass.

12. The method of claim 1 wherein said liquid or gel ranging from completely aqueous to completely non-aqueous in composition contains between 50% and 90% water by mass.

13. The method of claim 1 wherein said liquid or gel ranging from completely aqueous to completely non-aqueous in composition contains between 20% and 100% of a compound selected from the group consisting of: oils, fats, waxes, alcohols, glycols, esters, and ethers.

14. The method of claim 1 wherein said discrete small volume of a liquid or gel ranging from completely aqueous to completely non-aqueous in composition, contains one or more compounds selected from the group consisting of: carbohydrates; salts; proteins; lipids; vitamins; amino acids; plant, animal parts; insect parts; animal extracts; insect extracts; animal by-products; insect by-products; coloring agents; flavorings; thickeners; emulsifiers; drugs; pharmaceuticals, preservatives; pheromones; kairomones; phagostimulants; and semiochemical attractants.

15. The method of claim 1 wherein said discrete small volume of a liquid or gel ranging from completely: aqueous to completely non-aqueous in composition contains small living or dead organisms or microorganisms selected from the group consisting of: bacteria, fungi, viruses, molds, plankton, protozoa, nematodes, arthropods, yeasts, and algae; or eggs, spores, seeds, or parts thereof.

16. The method of claim 1 wherein said discrete small volume of a liquid or gel ranging from completely aqueous to completely non-aqueous in composition contains a pesticide, fungicide, herbicide, or insecticide.

17. The method of claim 15 wherein said small living or dead organism or microorganism is a entomopathogen.

18. The method of claim 1 wherein said step of generating a continuous coating, or layer of a polymerizable liquid surrounding a discrete small volume of a liquid or gel ranging from completely aqueous to completely non-aqueous in composition, wherein said layer of polymerizable liquid is substantially immiscible with said liquid or gel ranging from completely aqueous to completely non-aqueous in composition, and is effected by causing both the polymerizable liquid and a liquid or gel ranging from completely aqueous to completely non-aqueous in composition, to flow through nozzles having a predetermined geometry and arrangement.

19. The method of claim 1 wherein said polymerization occurs while the continuous coating, or layer of a polymerizable liquid surrounding a discrete small volume of a liquid or gel ranging from completely aqueous to completely non-aqueous in composition, is suspended in a liquid medium.

20. The method of claim 19 wherein said liquid medium is water, or an aqueous composition comprised primarily of water.

21. The capsules produced by the method of claim 1 which are composed of a polymeric shell, membrane, or coating, which surrounds a core composed of a liquid or gel ranging from completely aqueous to completely non-aqueous in composition.

22. The capsules of claim 21 which are generally spherical in nature and which have sizes ranging from 0.1 to 25 millimeters in diameter.

23. The capsules of claim 21 which are generally spherical in nature and which have sizes ranging from 0.5 to 10 millimeters in diameter.

24. The capsules of claim 21 which are generally spherical in nature and which have sizes ranging from 1 to 8 millimeters in diameter.

25. The capsules of claim 21 wherein said core composed of a liquid or gel ranging from completely aqueous to completely non-aqueous in composition, contains one or more compounds selected from the group consisting of: carbohydrates; salts; proteins; lipids; vitamins; amino acids; plant, animal parts; insect parts; animal extracts; insect extracts; animal by-products; insect by-products; coloring agents; flavorings; thickeners; emulsifiers; drugs; preservatives; pheromones; kairomones; phagostimulants; and semiochemical attractants.

26. The capsules of claim 21 wherein said core composed of a liquid or gel ranging from completely aqueous to completely non-aqueous in composition, contains one or more small living or dead organisms or microorganisms selected from the group which includes: bacteria, fungi, viruses, molds, plankton, protozoa, nematodes, arthropods, yeasts, and algae; or eggs, spores, seeds, and parts thereof.

27. The capsules of claim 21 wherein said core composed of a liquid or gel ranging from completely aqueous to completely non-aqueous in composition, contains a pesticide, fungicide, herbicide, or insecticide.

28. The capsules of claim 21 wherein said microorganism is a entomopathogen.

29. The capsules of claim 21 which contain a diet formulation used for the rearing of beneficial insects.

30. The capsules of claim 21 wherein said polymeric shell, membrane, or coating is sensitive to changes of pH; whereby said polymeric shell, membrane, or coating may swell, soften, rupture, or dissolve.

31. The capsules of claim 21 wherein said polymeric shell, membrane, or coating, is biodegradable.

32. A capsule comprising a solid polymer shell, membrane, or coating surrounding a discrete small volume of a liquid or gel ranging from completely aqueous to completely non-aqueous in composition, wherein said a liquid or gel ranging from completely aqueous to completely non-aqueous in composition contains between 90% and 100% water by mass.

33. The method according to claim 1 wherein said polymerizable liquid comprises acrylic acid, methacrylic acid, methyl acrylate, ethyl acrylate, propyl acrylate, n-butyl acrylate, pentyl acrylate, hexyl acrylate, 2-ethylhexyl acrylate, heptyl acrylate, octyl acrylate, nonyl acrylate, decyl acrylate, dodecyl acrylate, tetradecyl acrylate, hexadecyl acrylate, isopropyl acrylate, isobutyl acrylate, sec-butyl acrylate, 2-methylbutyl acrylate, 3-methylbutyl acrylate, 1-ethylpropyl acrylate, 2-methylpentyl acrylate, 2-ethylbutyl acrylate, 1,3-dimethylbutyl acrylate, 1-methylhexyl acrylate, 2-ethylhexyl acrylate, 1-methylheptyl acrylate, 4-ethyl-1-methyloctyl acrylate, 4-ethyl-1,1-isobutyloctyl acrylate, allyl acrylate, 2-methylallyl acrylate, 1-methylallyl acrylate, 2-butenyl acrylate, 1,3-dimethyl-3-dibutenyl acrylate, 3,7-dimethyl-7-octenyl acrylate, 3,7-dimethyl-2,6-octadienyl acrylate, 3,7-dimethyl-6-octenyl acrylate, tert-butyl acrylate, methyl methacrylate, ethyl methacrylate, n-propyl methacrylate, isopropyl methacrylate, n-butyl methacrylate, isobutyl methacrylate, sec-butyl methacrylate, tert-butyl methacrylate, n-hexyl methacrylate, n-octyl methacrylate, isooctyl methacrylate, decyl methacrylate, n-dodecyl methacrylate, n-tetradecyl methacrylate, n-hexadecyl methacrylate, 2-ethylhexyl methacrylate, allyl methacrylate, oleyl methacrylate, 2-propynyl methacrylate, or mixtures thereof.

34. A method of encapsulating a discrete small volume of a liquid or gel ranging from completely aqueous to completely non-aqueous in composition, which comprises:

(a) generating a continuous coating, or layer, of a polymerizable liquid which surrounds a discrete small volume of a liquid or gel ranging from completely aqueous to completely non-aqueous in composition, wherein said layer of polymerizable liquid is substantially immiscible with said liquid or gel ranging from completely aqueous to completely non-aqueous in composition and, (b) inducing polymerization of said polymerizable liquid; whereby a solid polymer shell, membrane, or coating is formed which surrounds said discrete small volume of a liquid or gel ranging from completely aqueous to completely non-aqueous in composition;

wherein said polymerization occurs while the continuous coating, or layer of a polymerizable liquid surrounding a discrete small volume of a liquid or gel ranging from completely aqueous to completely non-aqueous in composition, is suspended in a liquid medium.

* * * * *